United States Patent [19]

Comb et al.

[11] Patent Number: 5,322,785
[45] Date of Patent: Jun. 21, 1994

[54] PURIFIED THERMOSTABLE DNA POLYMERASE OBTAINABLE FROM THERMOCOCCUS LITORALIS

[75] Inventors: Donald G. Comb, Beverly; Francine Perler, Brookline; Rebecca Kucera, Beverly; William E. Jack, Rowley, all of Mass.

[73] Assignee: New England Biolabs, Inc., Beverly, Mass.

[21] Appl. No.: 686,340

[22] Filed: Apr. 17, 1991

Related U.S. Application Data

[63] Continuation-in-part of Ser. No. 626,057, Dec. 11, 1990, abandoned, which is a continuation-in-part of Ser. No. 513,994, Apr. 26, 1990, Pat. No. 5,210,036.

[51] Int. Cl.$^5$ .................. C12N 15/54; C12N 15/67; C12N 15/70; C12N 15/74
[52] U.S. Cl. .................. 435/194; 435/69.1; 435/193; 435/252.3; 435/252.33; 435/320.1; 536/23.2
[58] Field of Search .................. 435/194, 193, 69.1, 435/252.33, 320.1, 252.31; 536/27, 23.2

[56] References Cited

U.S. PATENT DOCUMENTS

| | | | |
|---|---|---|---|
| 4,652,639 | 3/1987 | Stabinsky | 536/23.1 |
| 4,683,195 | 7/1987 | Mullis et al. | 435/6 |
| 4,683,202 | 11/1990 | Mullis et al. | 435/91 |
| 4,800,159 | 1/1989 | Mullis et al. | 435/172.3 |
| 4,889,818 | 12/1989 | Gelfand et al. | 435/194 |
| 4,935,361 | 6/1990 | Lir et al. | 435/172.3 |
| 4,946,786 | 8/1990 | Tabor et al. | 435/194 |
| 4,952,496 | 8/1990 | Studiev et al. | 435/91 |
| 5,001,050 | 3/1991 | Blanco et al. | 435/5 |
| 5,002,875 | 3/1991 | Lacks et al. | 435/69.1 |
| 5,047,342 | 9/1991 | Chatterjee | 435/194 |
| 5,079,352 | 1/1992 | Gelfand et al. | 536/27 |
| 5,210,036 | 5/1993 | Comb et al. | 435/194 |
| 5,242,818 | 9/1993 | Oshima et al. | 435/194 |

FOREIGN PATENT DOCUMENTS 0258017 3/1988 European Pat. Off. .
455430A3 11/1991 European Pat. Off. .
92/09689 6/1993 PCT Int'l Appl. .

OTHER PUBLICATIONS

Mattila, *Nucleic Acids Research*, 19(18):4967–4973 (1991).
Saiki, et al., *Science*, 239:487–491 (1988).
Brock, et al., *Science*, 230:132–138 (1985).
Lehman, et al., *J. Biol. Chem.*, 233:163 (1958).
Wang, et al., *FASEB Journal*, 3:14–21 (1989).
Rossi, et al., *System Appl. Microbiol.*, 7:337–341 (1986).
Stetter, et al., *Journal of Chemical Technology and Biotechnology* 42:315–317 (1988).
Lundberg, et al., Derwent Abstract, Abstract No. 91-07714.
Tang, et al., Abstract Annual Meeting—Am. Soc. Microbiol. (90 Meet., p. 214) 1990.
Mathur, et al., Derwent Abstract, Abstract No. 92-02293.
Fiala, et al., *Archives of Microbiology*, 145(1):56–61 (1986).
Lundberg, et al., *The FASEB Journal*, 5(6): Abstract, Part III, p. A1549, Abstract No. 6841 (1991).
Bryant, et al., *The Journal of Biological Chemistry*, 264(9):5070–5079 (1989).

(List continued on next page.)

Primary Examiner—Robert A. Wax
Assistant Examiner—William W. Moore
Attorney, Agent, or Firm—David G. Conlin; Gregory D. Williams; David S. Resnick

[57] ABSTRACT

There is provided an extremely thermostable enzyme obtainable from *Thermococcus litoralis*. The thermostable enzyme has a molecular weight of about 90,000–95,000 daltons, a half-life of about 60 minutes at 100° C. in the absence of stabilizer, and a half-life of about 95 minutes at 100° C. in the presence of stabilizer, such as octoxynol (TRITON X-100) or bovine serum albumin. The thermostable enzyme possesses a 3'-5' proofreading exonuclease activity. The thermostable enzyme may be native or recombinant and may be used for second-strand cDNA synthesis in cDNA cloning, DNA sequencing, and DNA amplification.

39 Claims, 15 Drawing Sheets

ORGANIZATION OF THE T. litoralis DNA POLYMERASE GENE IN NATIVE DNA AND CLONE NEB671 AND NEB687

BOLD LINES REPRESENT T. litoralis DNA PRESENT IN EXPRESSION CLONE NEB671 AND CLONE NEB687

DASHED LINES REPRESENT CLONING JUNCTION SITES

HATCHED BOX REPRESENTS DELETED INTRON

OTHER PUBLICATIONS

Tabor, et al., *The Journal of Biological Chemistry*, 264(11):6447–6458 (1989).
Jung, et al., *Biochemical and Biophysical Research Communications*, 170(3):1294–1300 (1990).
Matsuda, et al., *FEBS Letters*, 126(1):111–113 (1981).
Hewick, et al., *The Journal of Biological Chemistry*, 256(15):7990–7997 (1981).
Xu, et al., *Analytical Biochemistry*, 170(1):19–30 (1988).
Stetter, et al., *FEMS Microbiology Reviews*, 75(1):117–124 (1990).
Mathur, et al., *The Journal of Cell Biology*, 115(3):80A, Abstract No. 463 (1991).
Advertisement, *Science*, 254(26) "Take the *Pyrococcus* Challenge" (1991).
Zillig, et al., *Systematic and Applied Microbiology*, 9(1–2):62–70 (1987).
Bessman, et al., J. Biol. Chem. (1957) 233:171–177.
Buttin and Kornberg, J. Biol. Chem. (1966) 241:5419–5427.
Brutlag, D. and Kornberg, A., J. Biol. Chem. (1972) 247:241–248.
Chang, L. M. S., J. Biol. Chem. (1977) 252:1873–1880.
Chien, A., et al., J. Bacteriol. (1976) 127:1550–1557.
Kaledin, et al., Biokhymiya (1980) 45:644–651 (Russian Text) English translation—Biochem. 45(4):494–501.
Lawyer, et al., J. Biol. Chem. (1989) 264:11, p. 6427–6437.
Bernad, et al., Cell (1989) 59:219.
Neuner, et al., Arch. Microbiol. 153:205–207 (1990).
Ruttimann, et al., J. Biochem. 149:41–46 (1985).
Elie, et al., J. Biochem. 178:619–626 (1989).
Bechtereva, et al., Nucleic Acid R s. 17(24): 10507 (1989).
Kjems, J., et al. 1989, *Canadian Journal of Microbiology*, 35(1):210–214.
Wich, G., et al., 1987, *The EMBO Journal*, 6(2):523–528.
Kuhsel, M. G., et al., 1990, *Science*, 250:1570–1573.
Xu, M.-Q., et al., 1990 *Science*, 250:1566–1570.
Belfort, M. 1991 *Cell* 64(1):9–11.
Kjems, J. et al. 1988 *Cell*, 54(3):693–703.
Bernstein, H. et al., 1989, *Journal of Bacteriology*, 171(5):2265–2270.
Goodrich-Blair, H., et al., 1990 *Cell*, 63(2):417–424.
Lundberg, K. S., et al., 1991 *Gene*, 108(1):1–6.
Perlman, P. S., et al., 1989, *Science*, 246:1106–1109.
Mathur, E. J., et al., 1991, Nacleic Acids Research 19(24):6952.

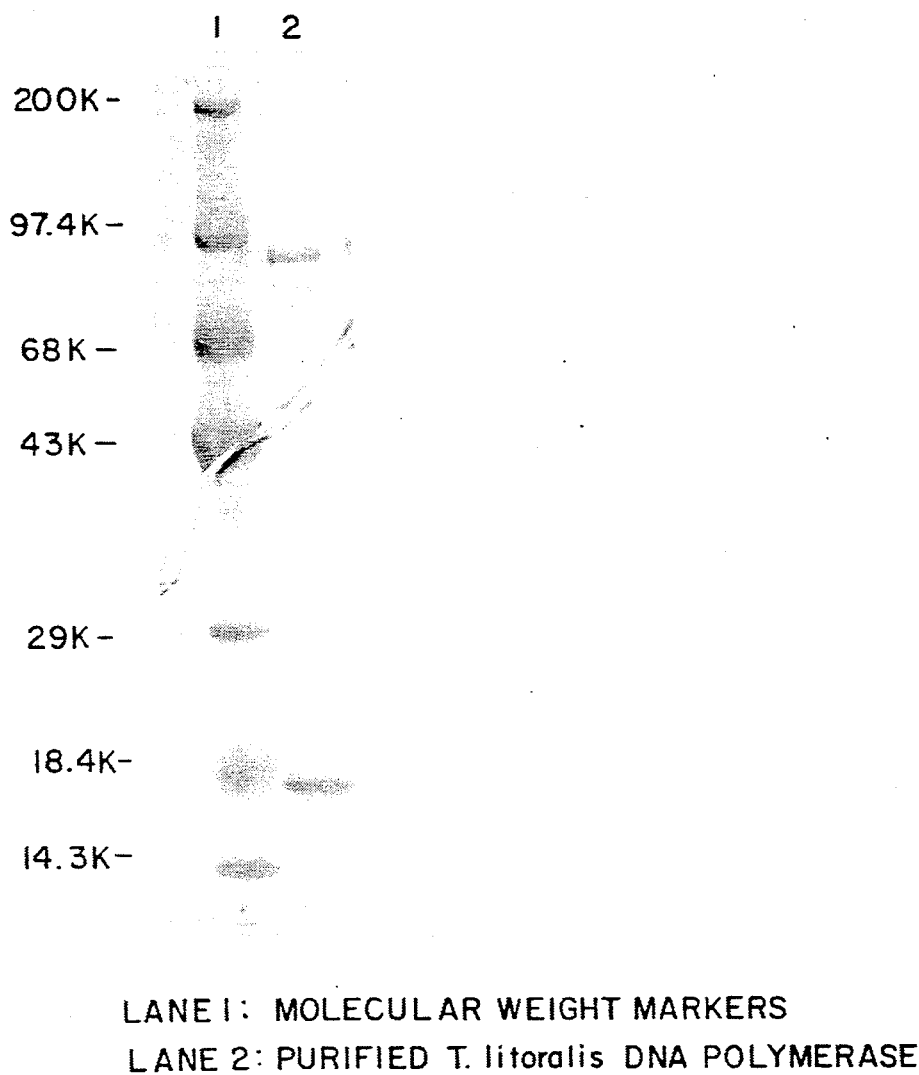
FIG. IA

SIZE DETERMINATION OF T. litoralis DNA POLYMERASE FUNCTIONS

THERMAL STABILITIES OF DNA POLYMERASES

RESPONSE OF DNA POLYMERASES TO THE PRESENCE OR ABSENSE OF DEOXYNUCLEOTIDES

```
GAATTCGCGA TAAAATCTAT TTTCTTCCTC CATTTTTCAA TTTCAAAAAC GTAAGCATGA      60
GCCAAACCTC TCGCCCTTTC TCTGTCCTTC CCGCTAACCC TCTTGAAAAC TCTCTCCAAA     120
GCATTTTTTG ATGAAAGCTC ACGCTCCTCT ATGAGGGTCA GTATATCTGC AATGAGTTCG     180
TGAAGGGTTA TTCTGTAGAA CAACTCCATG ATTTTCGATT TGGATGGGGG TTTAAAAATT     240
TGGCGGAACT TTTATTTAAT TTGAACTCCA GTTTATATCT GGTGGTATTT ATGATACTGG     300
ACACTGATTA CATAACAAAA GATGGCAAGC CTATAATCCG AATTTTTAAG AAAGAGAAACG    360
GGGAGTTTAA AATAGAACTT GACCCTCATT TTCAGCCCTA TATATATGCT CTTCTCAAAG     420
ATGACTCCGC TATTGAGGAG ATAAAGGCAA TAAAGGGCGA GAGACATGGA AAAACTGTGA     480
GAGTGCTCGA TGCAGTGAAA GTCAGGAAAA AATTTTTGGG AAGGAAGTT GAAGTCTGGA      540
AGCTCATTTT CGAGCATCCC CAAGACGTTC CAGCTATGCG GGGCAAAATA AGGGAACATC     600
CAGCTGTGGT TGACATTTAC GAATATGACA TACCCTTTGC CAAGCGTTAT CTCATAGACA     660
AGGGCTTGAT TCCATGGAG GGAGACGAGG AGCTTAAGCT CCTTGCCTTT GATATTGAAA      720
CGTTTTATCA TGAGGGAGAT GAATTTGGAA AGGGCGAGAT AATAATGATT AGTTATGCCG     780
ATGAAGAAGA GGCCAGAGTA ATCACATGGA AAAATATCGA TTTGCCGTAT GTCGATGTTG     840
TGTCCAATGA AAGAGAAATG ATAAAGCGTT TTGTTCAAGT TGTTAAAGAA AAAGACCCCG     900
ATGTGATAAT AACTTACAAT GGGGACAATT TTGATTTGCC GTATCTCATA AAACGGGCAG     960
AAAAGCTGGG AGTTCGGCTT GTCTTAGGAA GGGACAAAGA ACATCCCGAA CCCAAGATTC    1020
AGAGGATGGG TGATAGTTTT GCTGTGGAAA TCAAGGGTAG AATCCACTTT GATCTTTTCC    1080
```

FIG.6-1

```
CAGTTGTGCG AAGGACGATA AACCTCCCAA CGTATACGCT TGAGGCAGTT TATGAAGCAG    1140

TTTTAGGAAA AACCAAAAGC AAATTAGGAG CAGAGGAAAT TGCCGCTATA TGGGAAACAG    1200

AAGAAAGCAT GAAAAAACTA GCCCAGTACT CAATGGAAGA TGCTAGGGCA ACGTATGAGC    1260

TCGGGAAGGA ATTCTTCCCC ATGGAAGCTG AGCTGGCAAA GCTGATAGGT CAAAGTGTAT    1320

GGGACGTCTC GAGATCAAGC ACCGGCAACC TCGTGGAGTG GTATCTTTTA AGGGTGGCAT    1380

ACGCGAGGAA TGAACTTGCA CCGAACAAAC CTGATGAGGA AGAGTATAAA CGGCGCTTAA    1440

GAACAACTTA CCTGGAGGA TATGTAAAAG AGCCAGAAAA AGGTTTGTGG GAAAATATCA    1500

TTTATTTGGA TTTCCGCAGT CTGTACCCTT CAATAATAGT TACTCACAAC GTATCCCCAG    1560

ATACCCTTGA AAAAGAGGGC TGTAAGAATT ACGATGTTGC TCCGATAGTA GGATATAGGT    1620

TCTGCAAGGA CTTTCCGGGC TTTATTCCCT CCATACTCGG GGACTTAATT GCAATGAGGC    1680

AAGATATAAA GAAGAAAATG AAATCCACAA TTGACCCGAT CGAAAAGAAA ATGCTCGATT    1740

ATAGGCAAAG GGCTATTAAA TTGCTTGCAA ACAGCATCTT ACCCAACGAG TGGTTACCAA    1800

TAATTGAAAA TGGAGAAATA AAATTCGTGA AAATTGGCGA GTTTATAAAC TCTTACATGG    1860

AAAAACAGAA GGAAAACGTT AAACAGTAG AGAATACTGA AGTTCTCGAA GTAAACAACC    1920

TTTTTGCATT CTCATTCAAC AAAAAAATCA AAGAAAGTGA AGTCAAAAAA GTCAAGCCC    1980

TCATAAGACA TAAGTATAAA GGGAAAGCTT ATGAGATTCA GCTTAGCTCT GGTAGAAAAA    2040

TTAACATAAC TGCTGGCCAT AGTCTGTTTA CAGTTAGAAA TGGAGAAATA AAGGAAGTTT    2100

CTGGAGATGG GATAAAAGAA GGTGACCTTA TTGTAGCACC AAAGAAAATT AAACTCAATG    2160

AAAAAGGGGT AAGCATAAAC ATTCCGAGT TAATCTCAGA TCTTTCCGAG GAAGAAACAG     2220

CCGACATTGT GATGACGATT TCAGCCAAGG GCAGAAAGAA CTTCTTTAAA GGAATGCTGA    2280
```

FIG. 6-2

```
GAACTTTAAG GTGGATGTTT GGAGAAGAAA ATAGAAGGAT AAGAACATTT AATCGCTATT    2340

TGTTCCATCT CGAAAAACTA GGCCTTATCA AACTACTGCC CCGCGGATAT GAAGTTACTG    2400

ACTGGGAGAG ATTAAAGAAA TATAAACAAC TTTACGAGAA GCTTGCTGGA AGCGTTAAGT    2460

ACAACGGAAA CAAGAGAGAG TATTTAGTAA TGTTCAACGA GATCAAGGAT TTTATATCTT    2520

ACTTCCCACA AAAAGAGCTC GAAGAATGGA AAATTGGAAC TCTCAATGGC TTTAGAACGA    2580

ATTGTATTCT CAAAGTCGAT GAGGATTTTG GGAAGCTCCT AGGTTACTAT GTTAGTGAGG    2640

GCTATGCAGG TGCACAAAAA AATAAAACTG GTGGTATCAG TTATTCGGTG AAGCTTTACA    2700

ATGAGGACCC TAATGTTCTT GAGAGCATGA AAAATGTTGC AGAAAATTC TTTGGCAAGG    2760

TTAGAGTTGA CAGAAATTGC GTAAGTATAT CAAGAAGAT GGCATACTTA GTTATGAAAT    2820

GCCTCTGTGG AGCATTAGCC GAAAACAAGA GAATTCCTTC TGTTATACTC ACCTCTCCCG    2880

AACCGGTACG GTGGTCATTT TTAGAGGCGT ATTTTACAGG CGATGGAGAT ATACATCCAT    2940

CAAAAAGGTT TAGGCTCTCA ACAAAAAGCG AGCTCCTTGC AAATCAGCTT GTGTTCTTGC    3000

TGAACTCTTT GGGAATATCC TCTGTAAAGA TAGGCTTTGA CAGTGGGGTC TATAGAGTGT    3060

ATATAAATGA AGACCTGCAA TTCCACAAA CGTCTAGGGA GAAAACACA TACTACTCTA    3120

ACTTAATTCC CAAAGAGATC CTTAGGGACG TGTTTGGAAA AGAGTTCCAA AAGAACATGA    3180

CGTTCAAGAA ATTTAAAGAG CTTGTTGACT CTGGAAAACT TAACAGGGAG AAAGCCAAGC    3240

TCTTGGAGTT CTTCATTAAT GGAGATATTG TCCTTGACAG AGTCAAAAGT GTTAAAGAAA    3300

AGGACTATGA AGGGTATGTC TATGACCTAA GCGTTGAGGA TAACGAGAAC TTTCTTGTTG    3360

GTTTTGGTTT GCTCTATGCT CACAACAGCT ATTACGGCTA TATGGGGTAT CCTAAGGCAA    3420

GATGGTACTC GAAGGAATGT GCTGAAAGCG TTACCGCATG GGGGAGACAC TACATAGAGA    3480
```

FIG. 6-3

```
TGACGATAAG AGAAATAGAG GAAAAGTTCG GCTTTAAGGT TCTTTATGCG GACAGTGTCT   3540

CAGGAGAAAG TGAGATCATA ATAAGGCAAA ACGGAAAGAT TAGATTTGTG AAAATAAAGG   3600

ATCTTTTCTC TAAGGTGGAC TACAGCATTG GCGAAAAAGA ATACTGCATT CTCGAAGGTG   3660

TTGAAGCACT AACTCTGGAC GATGACGGAA AGCTTGTCTG GAAGCCCGTC CCCTACGTGA   3720

TGAGGCACAG AGCGAATAAA AGAATGTTCC GCATCTGGCT GACCAACAGC TGGTATATAG   3780

ATGTTACTGA GGATCATTCT CTCATAGGCT ATCTAAACAC GTCAAAAACG AAAACTGCCA   3840

AAAAAATCGG GGAAAGACTA AAGGAAGTAA AGCCTTTTGA ATTAGGCAAA GCAGTAAAAT   3900

CGCTCATATG CCCAAATGCA CCGTTAAAGG ATGAGAATAC CAAAACTAGC GAAATAGCAG   3960

TAAAATTCTG GGAGCTCGTA GGATTGATTG TAGGAGATGG AAACTGGGGT GGAGATTCTC   4020

GTTGGGCAGA GTATTATCTT GGACTTTCAA CAGGCAAAGA TGCAGAAGAG ATAAAGCAAA   4080

AACTTCTGGA ACCCCTAAAA ACTTATGGAG TAATCTCAAA CTATTACCCA AAAAACGAGA   4140

AAGGGGACTT CAACATCTTG GCAAAGAGCC TTGTAAAGTT TATGAAAAGG CACTTTAAGG   4200

ACGAAAAAGG AAGACGAAAA ATTCCAGAGT TCATGTATGA GCTTCCGGTT ACTTACATAG   4260

AGGCATTTCT ACGAGGACTG TTTTCAGCTG ATGGTACTGT AACTATCAGG AAGGGAGTTC   4320

CAGAGATCAG GCTAACAAAC ATTGATGCTG ACTTTCTAAG GGAAGTAAGG AAGCTTCTGT   4380

GGATTGTTGG AATTTCAAAT TCAATATTTG CTGAGACTAC TCCAAATCGC TACAATGGTG   4440

TTTCTACTGG AACCTACTCA AAGCATCTAA GGATCAAAAA TAAGTGGCGT TTTGCTGAAA   4500

GGATAGGCTT TTTAATCGAG AGAAAGCAGA AGAGACTTTT AGAACATTTA AAATCAGCGA   4560

GGGTAAAAAG GAATACCATA GATTTTGGCT TTGATCTTGT GCATGTGAAA AAAGTCGAAG   4620
```

FIG. 6-4

```
AGATACCATA CGAGGGTTAC GTTTATGACA TTGAAGTCGA AGAGACGCAT AGGTTCTTTG     4680

CAAACAACAT CCTGGTACAC AATACTGACG GCTTTTATGC CACAATACCC GGGGAAAAGC     4740

CTGAACTCAT TAAAAGAAA GCCAAGGAAT TCCTAAACTA CATAAACTCC AAACTTCCAG      4800

GTCTGCTTGA GCTTGAGTAT GAGGGCTTTT ACTTGAGAGG ATTCTTTGTT ACAAAAAAGC    4860

GCTATGCAGT CATAGATGAA GAGGGCAGGA TAACAACAAG GGGCTTGGAA GTAGTAAGGA    4920

GAGATTGGAG TGAGATAGCT AAGGAGACTC AGGCAAAGGT TTTAGAGGCT ATACTTAAAG    4980

AGGGAAGTGT TGAAAAAGCT GTAGAAGTTG TTAGAGATGT TGTAGAGAAA ATAGCAAAAT    5040

ACAGGGTTCC ACTTGAAAAG CTTGTTATCC ATGAGCAGAT TACCAGGGAT TTAAAGGACT    5100

ACAAAGCCAT TGGCCCTCAT GTCGCGATAG CAAAAAGACT TGCCGCAAGA GGGATAAAAG    5160

TGAAACGGG CACAATAATA AGCTATATCG TTCTCAAAGG GAGCGGAAAG ATAAGCGATA     5220

GGGTAATTTT ACTTACAGAA TACGATCCTA GAAAACACAA GTACGATCCG GACTACTACA    5280

TAGAAAACCA AGTTTTGCCG GCAGTACTTA GGATACTCGA AGCGTTTGGA TACAGAAAGG    5340

AGGATTTAAG GTATCAAAGC TCAAAACAAA CCGGCTTAGA TGCATGGCTC AAGAGGTAGC    5400

TCTGTTGCTT TTTAGTCCAA GTTTCTCCGC GAGTCTCTCT ATCTCTCTTT TGTATTCTGC    5460

TATGTGGTTT TCATTCACTA TTAAGTAGTC CGCCAAAGCC ATAACGCTTC CAATTCCAAA    5520

CTTGAGCTCT TTCCAGTCTC TGGCCTCAAA TTCACTCCAT GTTTTGGAT CGTCGCTTCT     5580

CCCTCTTCTG CTAAGCCTCT CGAATCTTTT TCTTGGCGAA GAGTGTACAG CTATGATGAT    5640

TATCTCTTCC TCTGGAAACG CATCTTTAAA CGTCTGAATT TCATCTAGAG ACCTCACTCC    5700

GTCGATTATA ACTGCCTTGT ACTTCTTTAG TAGTTCTTTT ACCTTTGGGA TCGTTAATTT    5760

TGCCACGGCA TTGTCCCCAA GCTCCTGCCT AAGCTGAATG CTCACACTGT TCATACCTTC    5820

GGGAGTTCTT GGGATCC                                                   5837
```

Region III:       ASP --- --- GLN --- ALA --- LYS --- --- ASN SER --- TYR GLY --- --- GLY Ile ALA --- --- --- THR --- --- GLY ARG Left Junction:    ASP TYR ARG GLN ARG ALA ILE LYS LEU LEU ALA ASN SER ILE LEU PRO ASN GLU Right Junction:                                    LEU LEU TYR ALA HIS ASN SER TYR GLY TYR MET GLY Ile ALA GLU SER VAL THR ALA TRP GLY ARG

FIG. 7 nt 1721  CGAAAGAAA ATGCTCGATT ATAGGCAAAG GCCTATTAAA TTGCTTGCAA ACAGCATCTT ACCC....

nt 3375                                          ...TATGCTCACA ACAGCTATTA CGGCTATATG GGGTATCCTAA...

5'       CGAAAGAAA ATGCTCGATT ATAGGCAAAG GCCTATTAAA TTGCTAGCAA ACAGCTATTA CGGCTATATG GGGTACCC 3'

3'       TAGCTTTCTTT TACGAGCTAA TATCCGTTTC CGGATAATTT AACGATCGTT TGTCGATAAT GCCGATATAC CCCATGGGATT 5'

FIG. 12

PURIFIED THERMOSTABLE DNA POLYMERASE OBTAINABLE FROM THERMOCOCCUS LITORALIS

CROSS-REFERENCE TO RELATED APPLICATIONS

The present application is a continuation-in-part of U.S. application Ser. No. 07/626,057 filed Dec. 11, 1990, now abadnoned, which is a continuation-in-part of U.S. application No. 07/513,994 filed Apr. 26, 1990, now U.S. Pat. No. 5,210,036, issued May 11, 1990.

FIELD OF THE INVENTION

The present invention relates to an extremely thermostable enzyme. More specifically, it relates to a thermostable DNA polymerase obtainable from *Thermococcus litoralis*.

BACKGROUND OF THE INVENTION

DNA polymerases are a family of enzymes involved in DNA repair and replication. Extensive research has been conducted on the isolation of DNA polymerases from mesophilic microorganisms such as *E. coli*. See, for example, Bessman, et al., *J. Biol. Chem.* (1957) 233:171–177 and Buttin and Kornberg *J. Biol. Chem.* (1966) 241:5419–5427.

Examples of DNA polymerases isolated from *E. coli* include *E. coli* DNA polymerase I, Klenow fragment of *E. coli* DNA polymerase I and T4 DNA polymerase. These enzymes have a variety of uses in recombinant DNA technology including, for example, labelling of DNA by nick translation, second-strand cDNA synthesis in cDNA cloning, and DNA sequencing. See Maniatis, et al., *Molecular Cloning: A Laboratory Manual* (1982). Recently, U.S. Pat. Nos. 4,683,195, 4,683,202 and 4,800,159 disclosed the use of the above enzymes in a process for amplifying, detecting, and/or cloning nucleic acid sequences. This process, commonly referred to as polymerase chain reaction (PCR), involves the use of a polymerase, primers and nucleotide triphosphates to amplify existing nucleic acid sequences.

The DNA polymerases discussed above possess a 3'-5' exonuclease activity which provides a proofreading function that gives DNA replication much higher fidelity than it would have if synthesis were the result of only a one base-pairing selection step. Brutlag, D. and Kornberg, A., *J. Biol. Chem.*, (1972) 247:241–248. DNA polymerases with 3'-5' proofreading exonuclease activity have a substantially lower base incorporation error rate when compared with a non-proofreading exonuclease-possessing polymerase. Chang, L. M. S., *J. Biol. Chem.*, (1977) 252:1873–1880.

Research has also been conducted on the isolation and purification of DNA polymerases from thermophiles, such as *Thermus aquaticus*. Chien, A., et al. *J. Bacteriol.* (1976) 127:1550–1557, discloses the isolation and purification of a DNA polymerase with a temperature optimum of 80° C. from *T. aquaticus* YT1 strain. The Chien, et al., purification procedure involves a four-step process. These steps involve preparation of crude extract, DEAE-Sephadex chromatography, phosphocellulose chromatography, and chromatography on DNA cellulose. Kaledin, et al., *Biokhymiyay* (1980) 45:644–651 also discloses the isolation and purification of a DNA polymerase from cells of *T. aquaticus* YT1 strain. The Kaledin, et al. purification procedure involves a six-step process. These steps involve isolation of crude extract, ammonium sulfate precipitation, DEAE-cellulose chromatography, fractionation on hydroxyapatite, fractionation on DEAE-cellulose, and chromatography on single-strand DNA-cellulose.

U.S. Pat. No. 4,889,818 discloses a purified thermostable DNA polymerase from *T. aquaticus,* Taq polymerase, having a molecular weight of about 86,000 to 90,000 daltons prepared by a process substantially identical to the process of Kaledin with the addition of the substitution of a phosphocellulose chromatography step in lieu of chromatography on single-strand DNA-cellulose. In addition, European Patent Application 0258017 discloses Taq polymerase as the preferred enzyme for use in the PCR process discussed above.

Research has indicated that while the Taq DNA polymerase has a 5'-3' polymerase-dependent exonuclease function, the Taq DNA polymerase does not possess a 3'-5' proofreading exonuclease function. Lawyer, F. C., et al. *J. Biol. Chem.*, (1989) 264:11, p. 6427–6437. Bernad, A., et al. *Cell* (1989) 59:219. As a result, Taq DNA polymerase is prone to base incorporation errors, making its use in certain applications undesirable. For example, attempting to clone an amplified gene is problematic since any one copy of the gene may contain an error due to a random misincorporation event. Depending on where in the replication cycle that error occurs (e.g., in an early replication cycle), the entire DNA amplified could contain the erroneously incorporated base, thus, giving rise to a mutated gene product. Furthermore, research has indicated that Taq DNA polymerase has a thermal stability of not more than several minutes at 100° C.

Accordingly, there is a desire in the art to obtain and produce a purified, highly thermostable DNA polymerase with 3'-5' proofreading exonuclease activity, that may be used to improve the DNA polymerase processes described above.

SUMMARY OF THE INVENTION

In accordance with the present invention, there is provided a thermostable enzyme obtainable from *T. litoralis* which catalyzes the polymerization of DNA. The thermostable enzyme obtainable from *T. litoralis* is a DNA polymerase which has an apparent molecular weight of about 90,000–95,000 daltons, a half-life of about 60 minutes at 100° C. in the absence of a stabilizer, and a half-life of about 95 minutes at 100° C. in the presence of a stabilizer such as octoxynol (TRITON X-100) or bovine serum albumin.

The DNA encoding the 90,000–95,000 daltons thermostable DNA polymerase obtainable from *T. litoralis* has been isolated and provides another means to obtain the thermostable enzyme of the present invention.

The *T. litoralis* DNA polymerase possesses 3'-5' proofreading exonuclease activity. This is the first instance of an extreme thermophilic polymerase possessing this proofreading activity. As a result, *T. litoralis* DNA polymerase has a much higher fidelity than a thermostable polymerase with no 3'-5' proofreading exonuclease function, such as Taq polymerase. In addition, the *T. litoralis* DNA polymerase has a substantially greater thermal stability or half life at temperatures from 96° C. to 100° C. than the Taq polymerase. Finally, when used in DNA replication such as the above-described PCR reaction, the *T. litoralis* DNA polymerase is superior to Taq polymerase at amplifying smaller amounts of target DNA in fewer cycle numbers.

BRIEF DESCRIPTION OF DRAWINGS

FIG. 1A is a photograph of the SDS-polyacrylamide gel of example 1.

FIGS. 6-1 through 6-5 collectively depict a partial nucleotide sequence of the 14 kb BamHI restriction fragment of bacteriophage NEB619 inclusive of the 1.3 kb, 1.6 kb and 1.9 kb Eco RI fragments and part of the Eco RI/BamHI fragment.

FIG. 7 is a comparison of the amino acids in the DNA polymerase consensus homology region III with the amino acids of the *T. litoralis* homology island III.

FIG. 12 is a nucleotide sequence of the primers used in Example III.

DETAILED DESCRIPTION OF THE PREFERRED EMBODIMENTS

Figure 1B:
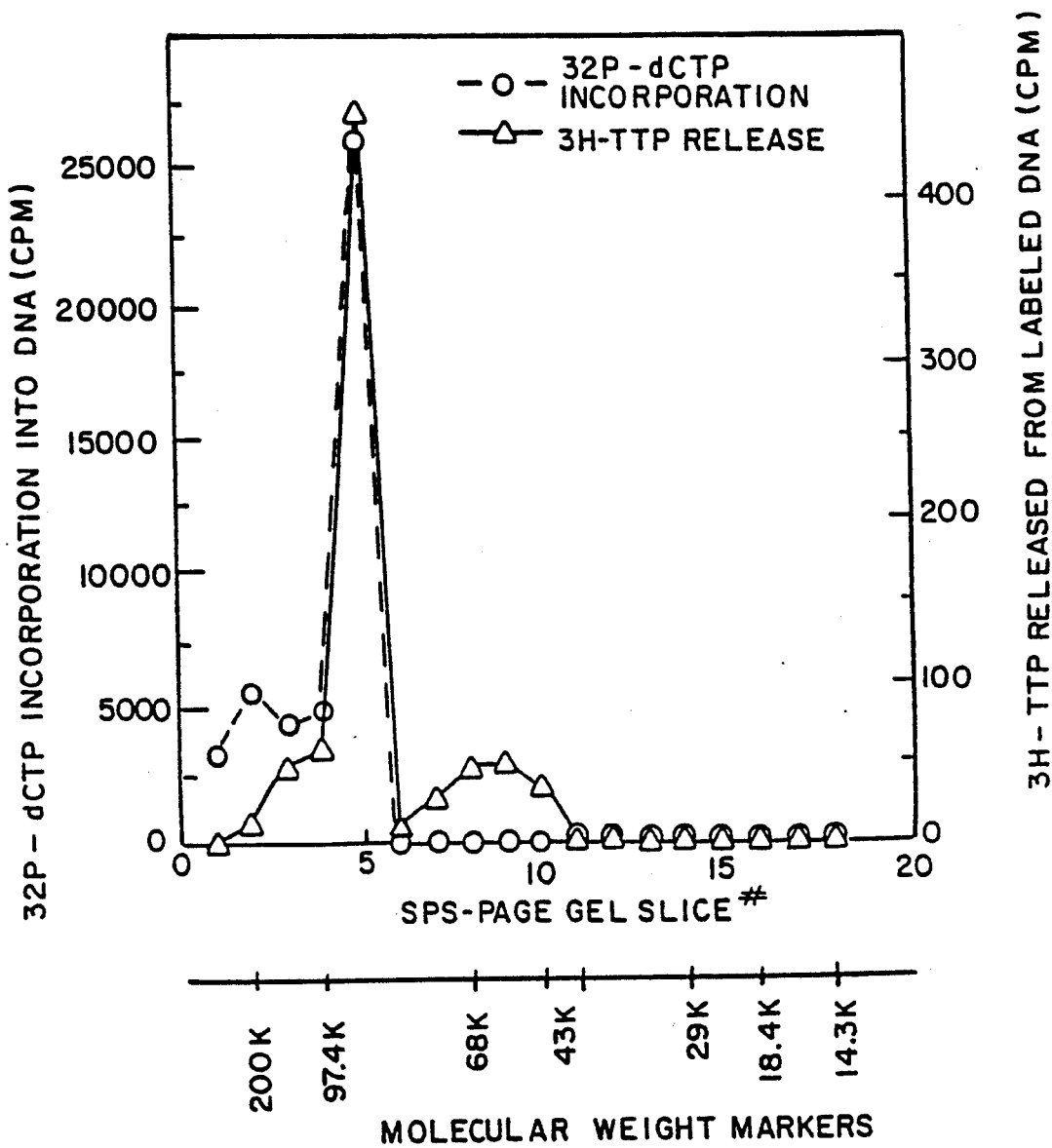
FIG. 1B is a graph showing the polymerase activity and exonuclease activity of the proteins eluted from lane 2 of the gel in FIG. 1A.
Figure 2:
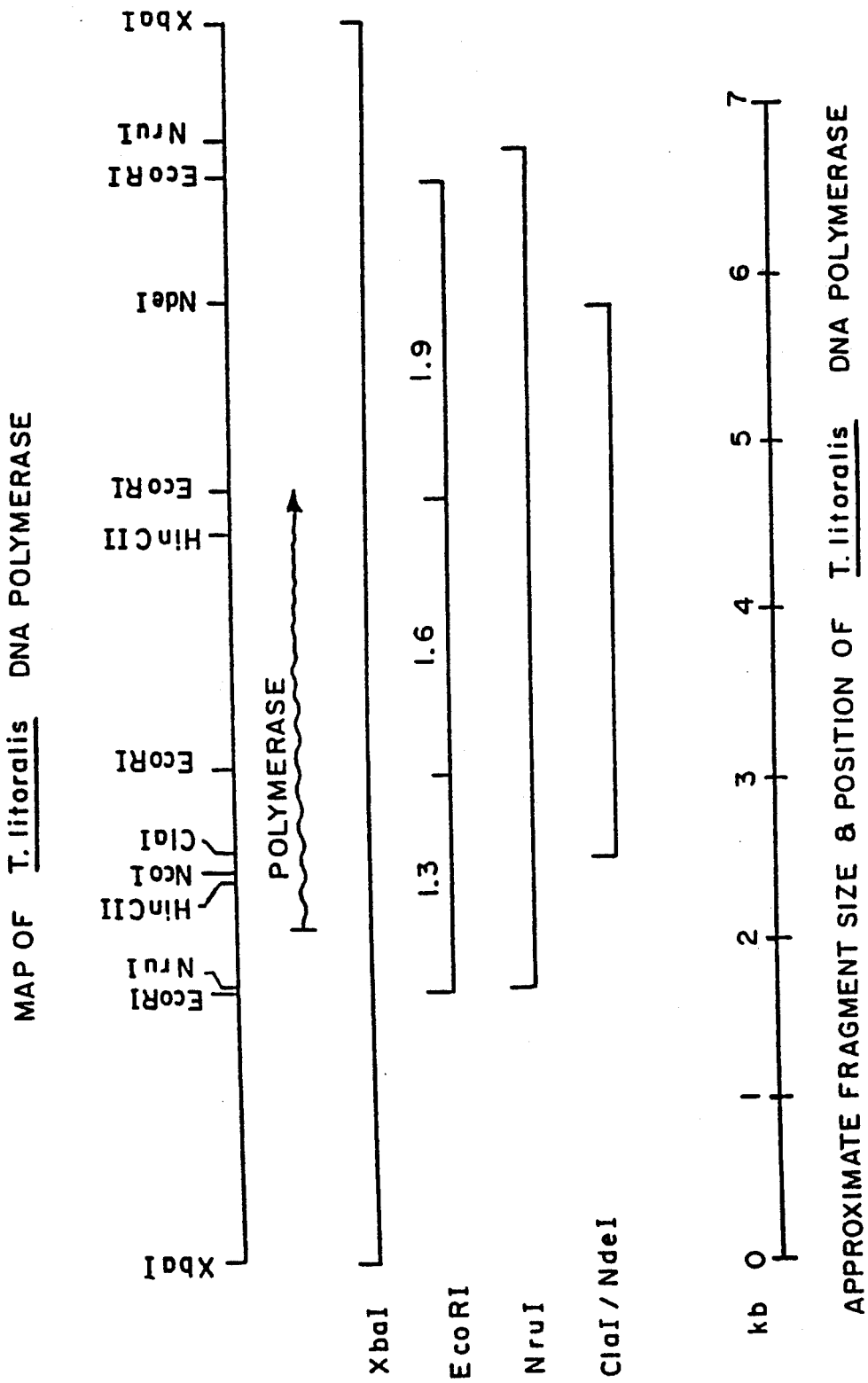
FIG. 2 is a restriction site map of the Xba fragment containing the gene encoding the *T. litoralis* DNA Polymerase which is entirely contained within the BamHI fragment of bacteriophage NEB 619.
Figure 3:
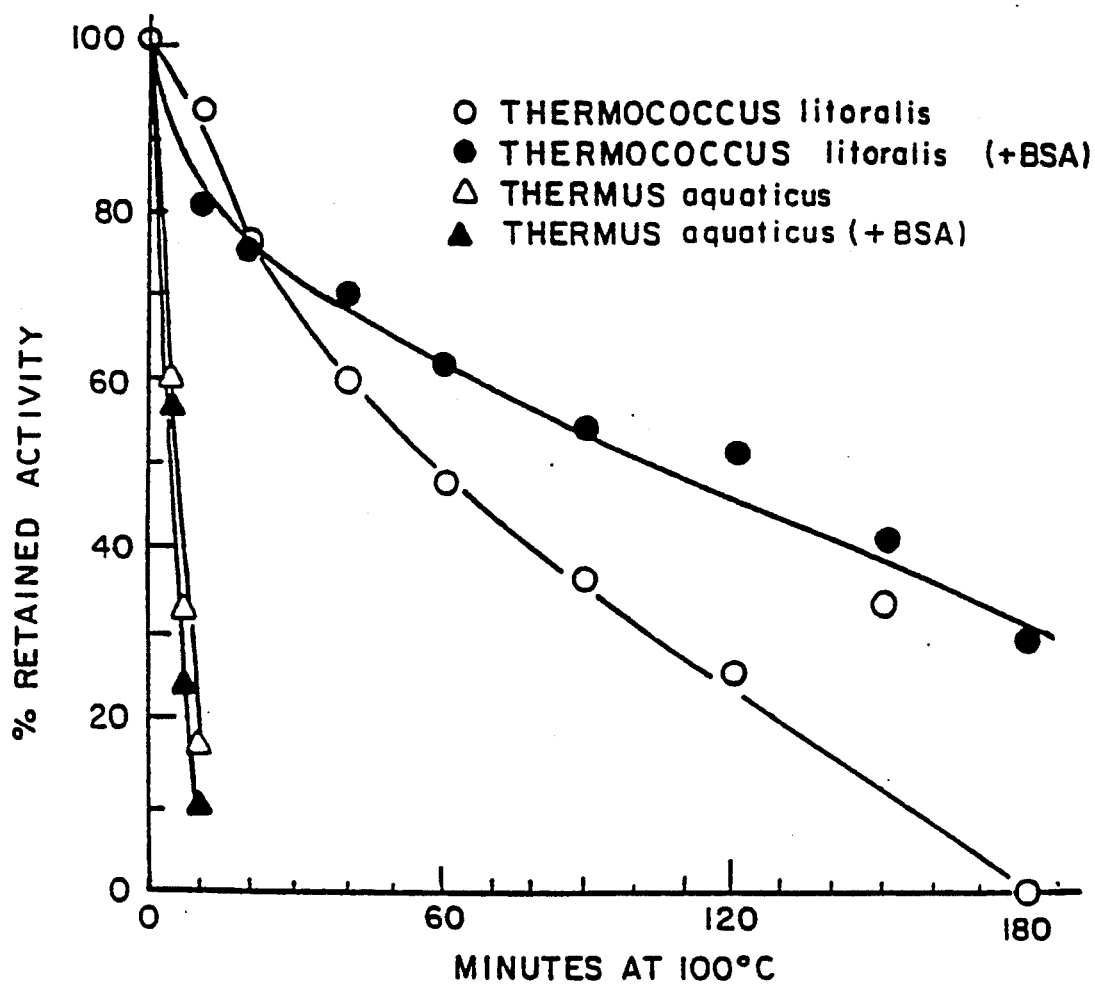
FIG. 3 is a graph showing the half-life of the *T. litoralis* DNA polymerase and the Taq DNA polymerase at 100° C.
Figure 4:
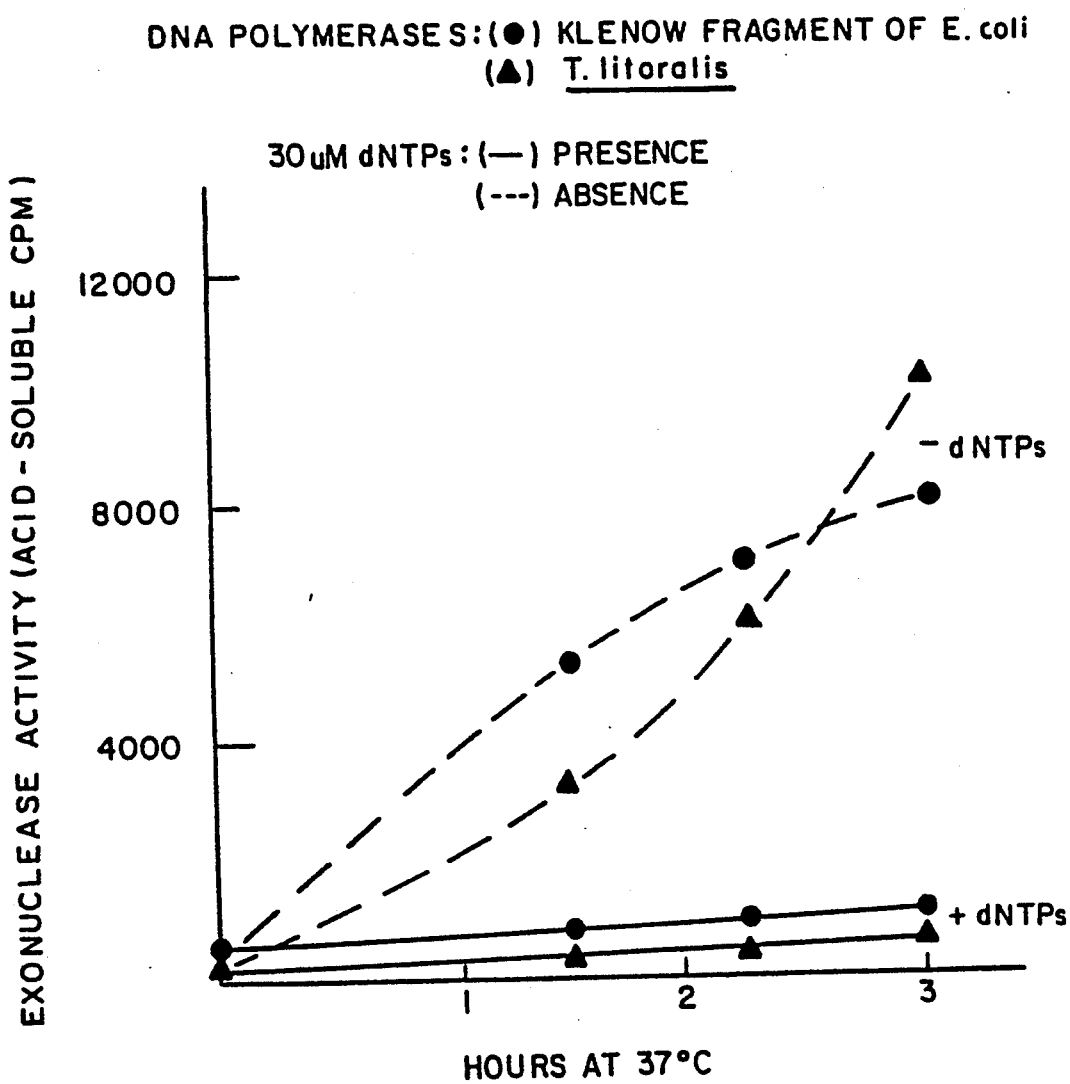
FIG. 4 is a graph showing the response of *T. litoralis* DNA polymerase and Klenow fragment to the presence or absence of deoxynucleotides.
Figure 5:
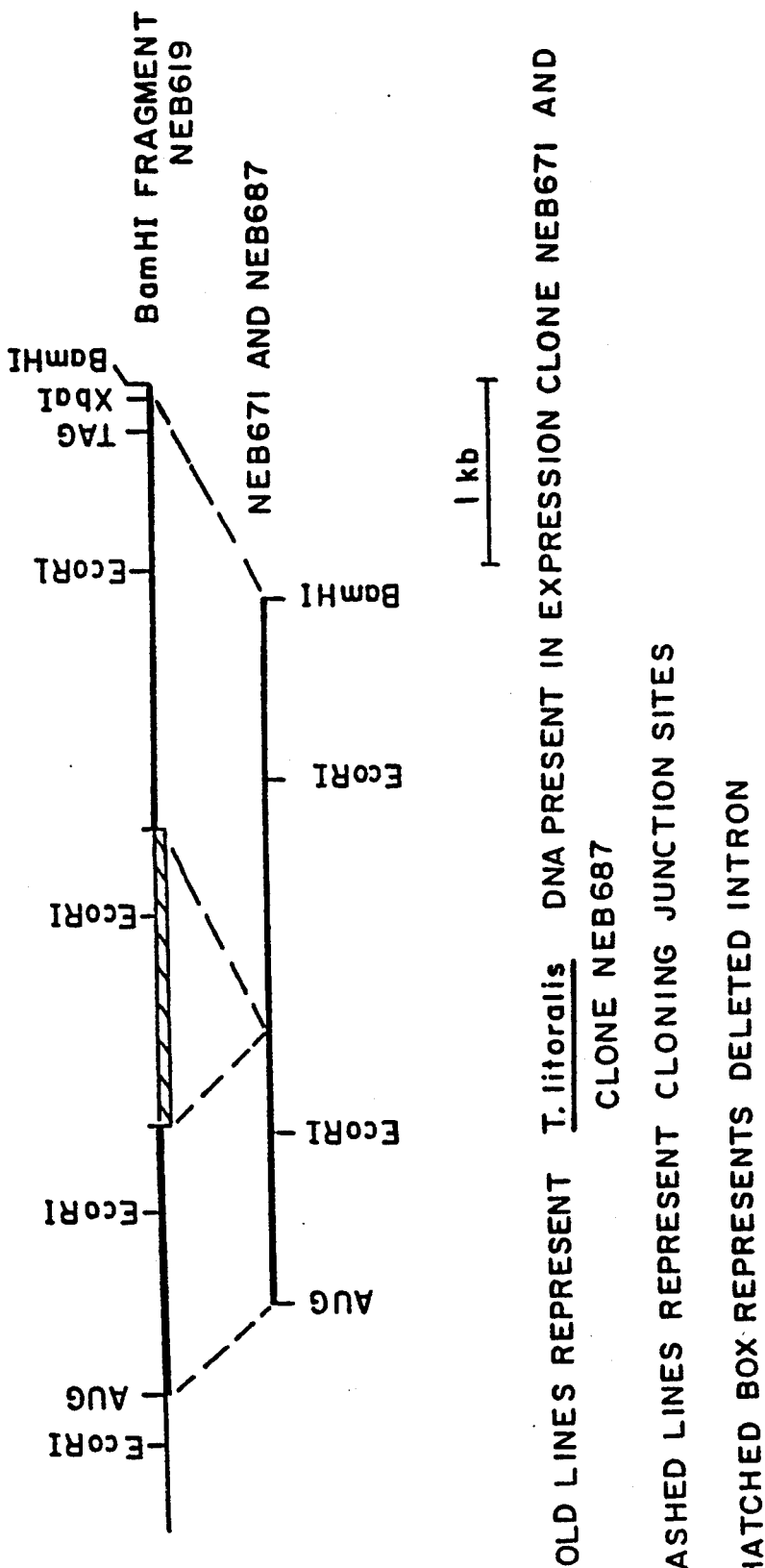
FIG. 5 is a restriction site map showing the organization of the *T. litoralis* DNA polymerase gene in native DNA (BamHI fragment of NEB 619) and in *E. coli* NEB671 and NEB687.
Figure 8:
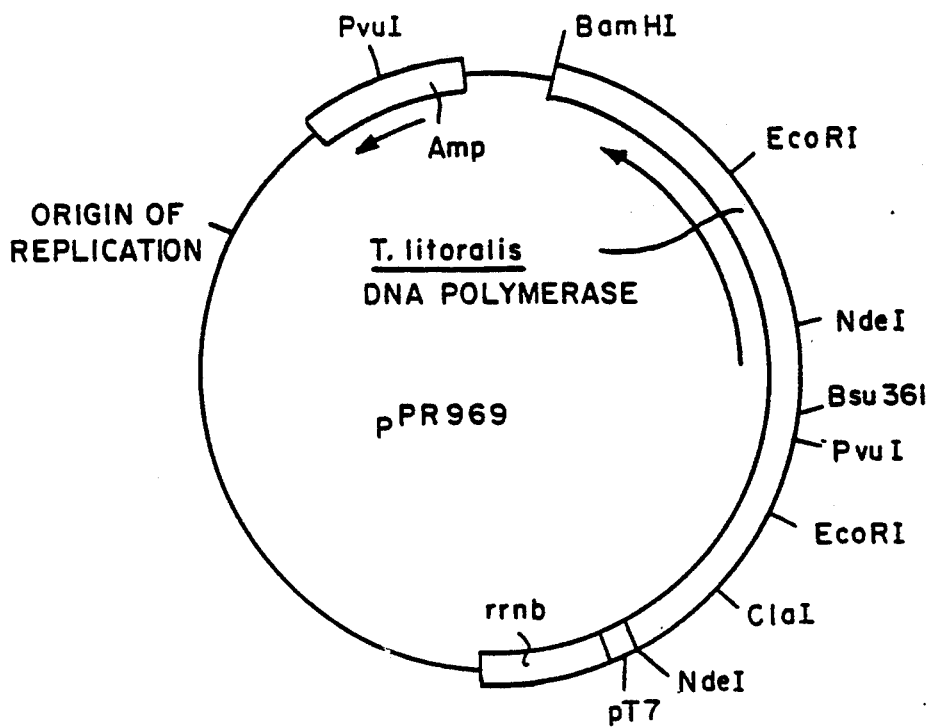
FIG. 8 are representations of the vectors
Figure 9:
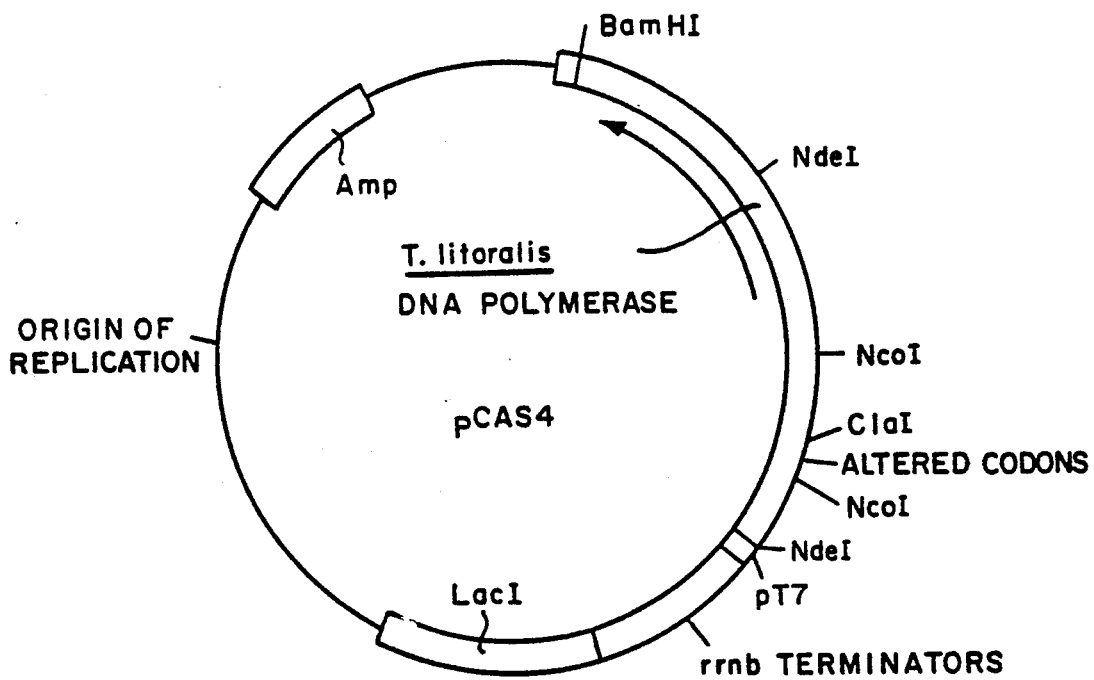
FIG. 9 & pPR969 and pCAS4 and V174-1B1.
Figure 10:
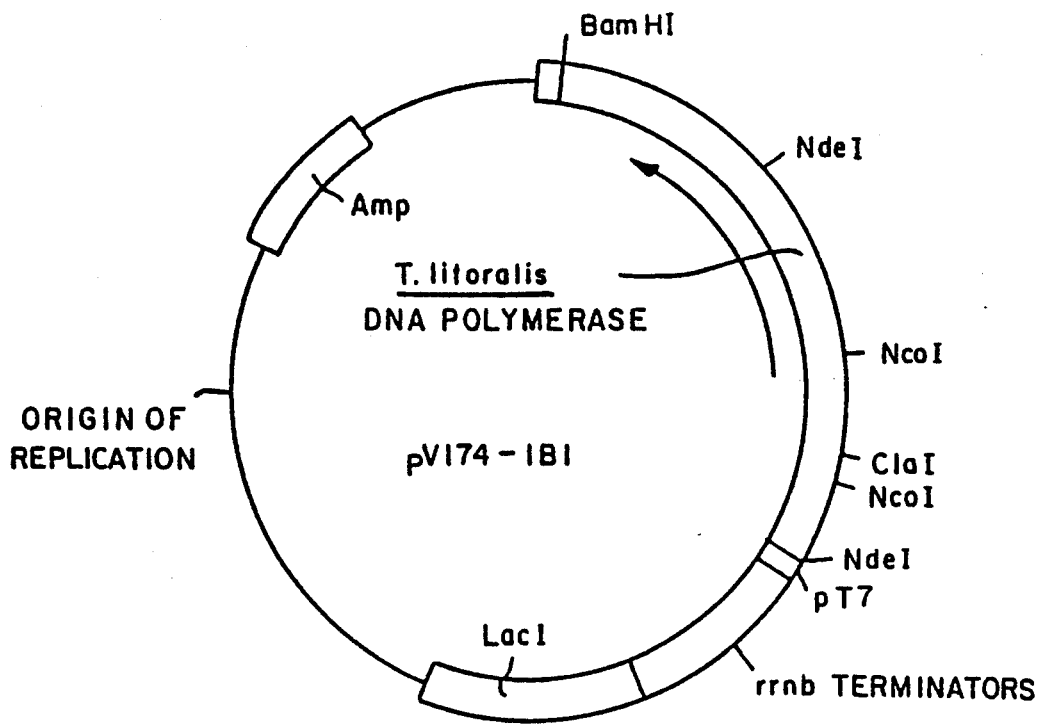
FIG. 10 respectively.
Figure 11:
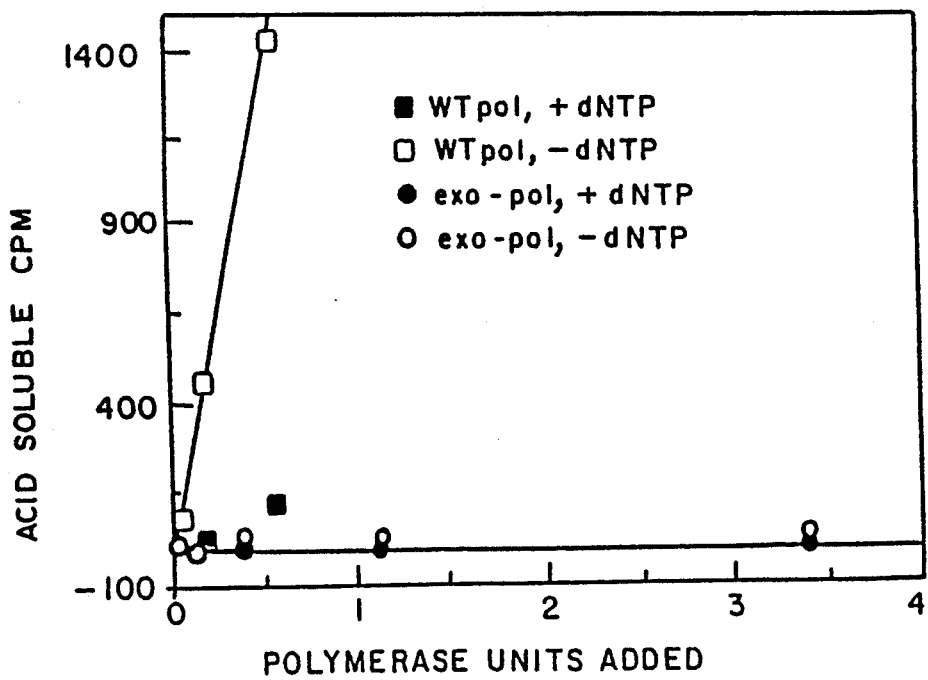
FIG. 11 is a graph illustrating the *T. litoralis* DNA polymerase variant constructed in Example VI lacks detectable 3' to 5' exonuclease activity.

The preferred thermostable enzyme herein is a DNA polymerase obtainable from *T. litoralis* strain NS-C (DSM No. 5473). *T. litoralis* was isolated from a submarine thermal vent near Naples, Italy in 1985. This organism, *T. litoralis* is an extremely thermophilic, sulfur metabolizing, archaebacteria, with a growth range between 55° C. and 98° C. Neuner, et al., *Arch. Microbiol.* (1990) 153:205-207.

For recovering the native protein, *T. litoralis* may be grown using any suitable technique, such as the technique described by Belkin, et al., *Arch. Microbiol.* (1985) 142:181-186, the disclosure of which is incorporated by reference.

After cell growth, one preferred method for isolation and purification of the enzyme is accomplished using the multi-step process as follows.

First, the cells, if frozen, are thawed, suspended in a suitable buffer such as buffer A (10 mM KPO4 buffer, pH 7.4; 1.0 mM EDTA, 1.0 mM beta-mercaptoethanol), sonicated and centrifuged. The supernatant is then passed through a column which has a high affinity for proteins that bind to nucleic acids such as Affigel blue column (Biorad). The nucleic acids present in supernatant solution of *T. litoralis* and many of the proteins pass through the column and are thereby removed by washing the column with several column volumes of low salt buffer at pH of about 7.0. After washing, the enzyme is eluted with a linear gradient such as 0.1 to 2.0M NaCl buffer A. The peak DNA polymerase activity is dialyzed and applied to phosphocellulose column. The column is washed and the enzyme activity eluted with a linear gradient such as 0.1 to 1.0M NaCl in buffer A. The peak DNA polymerase activity is dialyzed and applied to a DNA cellulose column. The column is washed and DNA polymerase activity is eluted with a linear gradient of 0.1 to 1.0M NaCl in buffer A. The fractions containing DNA polymerase activity are pooled, dialyzed against buffer A, and applied to a high performance liquid chromatography column (HPLC) mono-Q column (anion exchanger). The enzyme is again eluted with a linear gradient such as 0.05 to 1.0M NaCl in a buffer A. The fractions having thermostable polymerase activity are pooled, diluted and applied to HPLC mono-S column (cation exchanger). The enzyme is again eluted with a linear gradient such as 0.05 to 1.0M NaCl in buffer A. The enzyme is about 50% pure at this stage. The enzyme may further be purified by precipitation of a contaminating lower molecular weight protein by repeated dialysis against buffer A supplemented with 50 mM NaCl.

The apparent molecular weight of the DNA polymerase obtainable from *T. litoralis* is between about 90,000 to 95,000 daltons when compared with protein standards of known molecular weight, such as phosphorylase B assigned a molecular weight of 97,400 daltons. It should be understood, however, that as a protein from an extreme thermophile, *T. litoralis* DNA polymerase may electrophorese at an aberrant relative molecular weight due to failure to completely denature or other instrinsic properties. The exact molecular weight of the thermostable enzyme of the present invention may be determined from the coding sequence of the *T. litoralis* DNA polymerase gene. The molecular weight of the eluted product may be determined by any technique, for example, by SDS-polyacrylamide gel electrophoresis (SDS-PAGE) using protein molecular weight markers.

Polymerase activity is preferably measured by the incorporation of radioactively labeled deoxynucleotides into DNAse-treated, or activated, DNA; following subsequent separation of the unincorporated deoxynucleotides from the DNA substrate, polymerase activity is proportional to the amount of radioactivity in the acid-insoluble fraction comprising the DNA. Lehman, I. R., et al., *J. Biol. Chem.* (1958) 233:163, the disclosure of which is incorporated herein by reference.

The half-life of the DNA polymerase of the present invention at 100° C. is about 60 minutes. The thermal stability or half-life of the DNA polymerase is determined by preincubating the enzyme at the temperature of interest in the presence of all assay components (buffer, MgCl2, deoxynucleotides, and activated DNA) except the single radioactively-labeled deoxynucleotide. At predetermined time intervals, ranging from 4-180 minutes, small aliquots are removed, and assayed for polymerase activity using the method described above.

The half-life at 100° C. of the DNA polymerase can also be determined in the presence of stabilizers such as the nonionic detergent octoxynol, commonly known as TRITON X-100 (Rohm & Haas Co.), or the protein bovine serum albumin (BSA). The non-ionic detergents polyoxyethylated (20) sorbitan monolaurate (Tween 20, ICI Americas Inc.) and ethoxylated alkyl Phenol (nonyl) (ICONOL NP-40, BASF Wyandotte Corp.) can also be used. Stabilizers are used to prevent the small amount of enzyme added to the reaction mixture from adhering to the sides of the tube or from changing its structural conformation in some manner that decreases its enzymatic activity. The half-life at 100° C. of the DNA polymerase obtainable from *T. litoralis* in the presence of the stabilizer TRITON X-100 or BSA is about 95 minutes.

The thermostable enzyme of this invention may also be produced by recombinant DNA techniques, as the gene encoding this enzyme has been cloned from *T. litoralis* genomic DNA. The complete coding sequence for the *T. litoralis* DNA polymerase can be derived from bacteriophage NEB 619 on an approximately 14 kb BamHI restriction fragment. This phage was deposited with the American Type Culture Collection (ATCC) on Apr. 24, 1990 and has Accession No. ATCC 40795.

The production of a recombinant form of *T. litoralis* DNA polymerase generally includes the following steps: DNA is isolated which encodes the active form of the polymerase, either in its native form or as a fusion with other sequences which may or may not be cleaved away from the native form of the polymerase and which may or may not effect polymerase activity. Next, the gene is operably linked to appropriate control sequences for expression in either prokaryotic or eukaryotic host/vector systems. The vector preferably encodes all functions required for transformation and maintenance in a suitable host, and may encode selectable markers and/or control sequences for *T. litoralis* polymerase expression. Active recombinant thermostable polymerase can be produced by transformed host cultures either continuously or after induction of expression. Active thermostable polymerase can be recovered either from within host cells or from the culture media if the protein is secreted through the cell membrane.

While each of the above steps can be accomplished in a number of ways, it has been found in accordance with the present invention that for cloning the DNA encoding *T. litoralis* DNA polymerase, expression of the polymerase from its own control sequences in *E. coli* results in instability of the polymerase gene, high frequency of mutation in the polymerase gene, slow cell growth, and some degree of cell mortality.

While not wishing to be bound by theory, it is believed that this instability is due at least in part to the presence of an intron that splits the *T. litoralis* DNA polymerase gene. Introns are stretches of intervening DNA which separate coding regions of a gene (the protein coding regions are called exons). Introns can contain nonsense sequences or can code for proteins. In order to make a functional protein, the intron must be spliced out of the pre-mRNA before translation of the mature mRNA into protein. Introns were originally identified in eukaryotes, but have been recently described in certain prokaryotes. See, Krainer and Maniatis (*Transcription and Splicing* (1988) B. D. Hames and D. M. Glover, eds. IRL Press, Oxford and Washington, D.C. pp. 131-206). When a gene with an intron is transcribed into mRNA the intron may self-splice out to form a mature mRNA or cellular factors may be required to remove the intron from the pre-mRNA. Id. Bacterial introns often require genus specific co-factors for splicing. For example, a Bacillus intron may not be spliced out in *E. coli*. Id.

However, there is some evidence that suggests that the intervening DNA sequence within the gene coding for the *T. litoralis* DNA polymerase is transcribed and translated, and that the peptide produced therefrom is spliced out at the protein level, not the mRNA level. Therefore, regardless of where the splicing event occurs, in accordance with the present invention, in order to express *T. litoralis* DNA polymerase in *E. coli*, it is necessary to delete the *T. litoralis* DNA polymerase intervening sequence prior to expression of the polymerase in an *E. coli* system. Of course, the recombinant vector containing the *T. litoralis* DNA polymerase gene could be expressed in systems which possess the appropriate factors for splicing the intron, for example, a Thermococcus system. It is also believed that the *T. litoralis* gene may be expressed in a mammalian expression system which has the appropriate factors to splice such an intron.

It is also preferable that *T. litoralis* thermostable polymerase expression be tightly controlled in *E. coli* during cloning and expression. Vectors useful in practicing the present invention should provide varying degrees of controlled expression of *T. litoralis* polymerase by providing some or all of the following control features: (1) promoters or sits of initiation of transcription, either directly adjacent to the start of the polymerase or as fusion proteins, (2) operators which could be used to turn gene expression on or off, (3) ribosome binding sites for improved translation, and (4) transcription or translation termination sites for improved stability. Appropriate vectors used in cloning and expression of *T. litoralis* polymerase include, for example, phage and plasmids. Example of phage include lambda gtll (Promega), lambda Dash (Stratagene) lambda ZapII (Stratagene). Examples of plasmids include pBR322, pBluescript (Stratagene), pSP73 (Promega), pGW7 (ATCC No. 40166), pET3A (Rosenberg, et al., *Gene,* (1987) 56:125-135), and pET11C (*Methods in Enzymology* (1990) 185:60-89).

Transformation and Infection

Standard protocols exist for transformation, phage infection and cell culture. Maniatis, et al., *Molecular Cloning: A Laboratory Manual* (1982). Of the numerous *E. coli* strains which can be used for plasmid transformation, the preferred strains include JM101 (ATCC No. 33876), XL1 (Stratagene), and RRI (ATCC No. 31343), and BL21(DE3) plysS (*Methods in Enzymology* (1990) supra). *E. coli* strain XL1, ER1578 and ER1458 (Raleigh, et al., N. A. Research (1988) 16:1563-1575) are among the strains that can be used for lambda phage, and Y1089 can be used for lambda gtll lysogeny. When preparing transient lysogens in Y1089 (Arasu, et al., *Experimental Parasitology* (1987) 64:281-289), a culture is infected With lambda gtll recombinant phage either by a single large dose of phage or by co-culturing with a lytic host. The infected Y1089 cells are preferably grown at 37° C. in the presence of the inducer IPTG resulting in buildup of recombinant protein within the lysis-defective host/phage system.

Construction of Genomic DNA Expression Library and Screening for Thermostable Polymerase The most common methods of screening for a gene of choice are (1) by hybridization to homologous genes from other organisms, (2) selection of activity by complementation of a host defect, (3) reactivity with specific antibodies, or (4) screening for enzyme activity. Antibody detection is preferred since it initially only requires expression of a portion of the enzyme, not the complete active enzyme. The instability of the *T. litor-*

*alis* polymerase gene in *E. coli* would have made success by other methods more difficult.

*T. litoralis* DNA can be used to construct genomic libraries as either random fragments or restriction enzyme fragments. The latter approach is preferred. Preferably, Eco RI partials are prepared from *T. litoralis* genomic DNA using standard DNA restriction techniques such as described in Maniatis, et al., *Molecular Cloning: A Laboratory Manual* (1982), the disclosure of which is incorporated herein by reference. Other restriction enzymes such as BamHI, NruI and XbaI can also be used.

Although methods are available to screen both plasmids and phage using antibodies (Young and Davis, *PNAS*, (1983) 80:1194–1198), in accordance with the present invention it has been found that phage systems tend to work better and are therefore preferred for the first libraries. Since it is uncertain whether *T. litoralis* control regions function in *E. coli*, phage vectors which supply all necessary expression control regions such as lambda gtll and lambda Zap II, are preferred. By cloning *T. litoralis* DNA into the Eco RI site of lambda gt11, *T. litoralis* polymerase may be expressed either as a fusion protein with beta-galactosidase or from its own endogenous promoter.

Once formed, the expression libraries are screened with mouse anti-*T. litoralis* DNA polymerase antiserum using standard antibody plaque hybridization procedures such as those described by Young and Davis, *PNAS* (1983), supra.

The mouse anti-*T. litoralis* DNA polymerase antiserum used to screen the expression libraries can be prepared using standard techniques, such as the techniques described in Harlow and Cane, *Antibodies: A Laboratory Manual* (1988) CSH Press, the disclosure of which is incorporated herein by reference. Since most sera react with *E. coli* proteins, it is preferable that the *T. litoralis* polymerase antisera be preabsorbed by standard methods against *E. coli* proteins to reduce background reactivity when screening expression libraries. Phage reacting with anti-*T. litoralis* polymerase antiserum are picked and plaque purified. Young and Davis, *PNAS* (1983), supra.

The *T. litoralis* DNA polymerase DNA, coding for part of the whole gene, can then be subcloned in, for example, pBR322, pBluescript, M13 or pUC19. If desired, the DNA sequence can be determined by, for example, the Sanger dideoxy chain-terminating method (Sanger, F., Nicklen, S. & Coulson, A. R. *PNAS* (1977) 74:5463–5467).

Identification of DNA Encoding and Expression of the *T. litoralis* DNA Polymerase Several methods exist for determining that the DNA sequence coding for the *T. litoralis* DNA polymerase has been obtained. These include, for example, comparing the amino-terminal sequence of the protein produced by the recombinant DNA to the native protein, or determining whether the recombinant DNA produces a protein which binds antibody specific for native *T. litoralis* DNA polymerase. In addition, research by Wang, et al., *FASEB Journal* (1989) 3:20 suggests that certain regions of DNA polymerase sequences are highly conserved among many species. As a result, by comparing the predicted amino acid sequence of the cloned gene with the amino acid sequence of known DNA polymerases, such as human DNA polymerase and *E. coli* phage T4 DNA polymerase, the identification of these islands of homology provides strong evidence that the recombinant DNA indeed encodes a DNA polymerase.

Once identified, the DNA sequence coding for the *T. litoralis* DNA polymerase, can be cloned into an appropriate expression vector such as a plasmid derived from *E. coli*, for example, pET3A, pBluescript or pUC19, the plasmids derived from the *Bacillus subtilis* such as pUB110, pTP5 and pC194, plasmids derived from yeast such as pSH19 and pSH15, bacteriophage such as lambda phage, bacteria such as *Agrobacterium tumefaciens*, animal viruses such as retroviruses and insect viruses such as Baculovirus.

As noted above, in accordance with the present invention, it has been found that DNA coding for *T. litoralis* DNA polymerase contains an 1614 bp intron or intervening sequence, spanning from nucleotides 1776 to 3389 in FIG. No. 6. Therefore, prior to overexpression in host cells such as *E. coli*, it is preferable to delete the DNA sequence coding for the intron. There are a number of approaches known in the art which can be used to delete DNA sequences and therefore splice out an intron in-vitro. One method involves identifying unique restriction enzyme sites in the coding region which are near the splice junction or area to be deleted. A duplex oligomer is synthesized to bridge the gap between the 2 restriction fragments. A 3-part ligation consisting of the amino end restriction fragment, the bridging oligo and the carboxy end restriction fragment yields an intact gene with the intron deleted.

Another method is a modification of the above-described method. The majority of the intron is deleted by cutting with restriction enzymes with unique site within the intron, but close to the coding sequence border. The linear plasmid containing a deletion of the majority of the intron is ligated together. Single strand phage are generated from the pBluescript vector recombinant by superinfection with the f1 helper phage IR1. A single strand oligomer is synthesized with the desired final sequence and is annealed to the partially deleted intron phage DNA. The remainder of the intron is thus looped out. By producing the original phage in *E. coli* strain CJ236 the Kunkel method of mutagenesis (*Methods in Enzymology* 154:367 (1987)) can be used to select for the full deleted intron contructs.

Yet another method which can be used to delete the intron uses DNA amplification. See, for example, Maniatis, et al., *Molecular Cloning: A Laboratory Manual*, (1989) Vol. 2, 2nd edition, the disclosure of which is herein incorporated by reference. Briefly, primers are generated to amplify and subsequently join the amino and carboxyl halves of the gene.

When an intron is deleted in-vitro, using the methods discussed above, the native splice junction may be unknown. Accordingly, one skilled in the art would predict that several possible artificial splice junctions exist that would result in the production of an active enzyme.

Once the intron is deleted, overexpression of the *T. litoralis* DNA polymerase can be achieved, for example, by separating the *T. litoralis* DNA polymerase gene from its endogenous control elements and then operably linking the polymerase gene to a very tightly controlled promoter such as a T7 expression vector. See, Rosenberg, et al., *Gene* (1987) 56:125–135, which is hereby incorporated by reference. Insertion of the strong promoter may be accomplished by identifying convenient restriction targets near both ends of the *T. litoralis* DNA polymerase gene and compatible restriction targets on the vector near the promoter, or generating restriction targets using site directed mutagenesis (Kunkel (1984), supra), and transferring the *T. litoralis* DNA polymerase gene into the vector in such an orientation as to be under transcriptional and translational control of the strong promoter.

*T. litoralis* DNA polymerase may also be overexpressed by utilizing a strong ribosome binding site placed upstream of the *T. litoralis* DNA polymerase gene to increase expression of the gene. See, Shine and Dalgarno, *Proc. Natl. Acad. Sci. USA* (1974) 71:1342-1346, which is hereby incorporated by reference.

The recombinant vector is introduced into the appropriate host using standard techniques for transformation and phage infection. For example, the calcium chloride method, as described by Cohen, S. N., *PNAS* (1972) 69:2110 is used for *E. coli*, the disclosure of which is incorporated by reference. The transformation of Bacillus is carried out according to the method of Chang, S., et al., *Molecular and General Genetics* (1979) 168:111, the disclosure of which is incorporated by reference. Transformation of yeast is carried out according to the method of Parent, et al., *Yeast* (1985) 1:83-138, the disclosure of which is incorporated by reference. Certain plant cells can be transformed with *Agrobacterium tumefaciens*, according to the method described by Shaw, C. H., et al., *Gene* (1983) 23:315, the disclosure of which is incorporated by reference. Transformation of animal cells is carried out according to, for example, the method described in *Virology* (1973) 52:456, the disclosure of which is incorporated by reference. Transformation of insect cells with Baculovirus is carried out according to, for example, the method described in *Biotechnology* (1988) 6:47, the disclosure of which is incorporated herein by reference.

The transformants are cultivated, depending on the host cell used, using standard techniques appropriate to such cells. For example, for cultivating *E. coli*, cells are grown in LB media (Maniatis, supra) at 30° C. to 42° C. to mid log or stationary phase.

The *T. litoralis* DNA polymerase can be isolated and purified from a culture of transformed host cells, for example, by either extraction from cultured cells or the culture solution.

When the *T. litoralis* DNA polymerase is to be extracted from a cultured cell, the cells are collected after cultivation by methods known in the art, for example, centrifugation. Then, the collected cells are suspended in an appropriate buffer solution and disrupted by ultrasonic treatment, lysozyme and/or freeze-thawing. A crude extract containing the *T. litoralis* DNA polymerase is obtained by centrifugation and/or filtration.

When the *T. litoralis* DNA polymerase is secreted into the culture solution, i.e., alone or as a fusion protein with a secreted protein such as maltose binding protein, the supernatant is separated from the cells by methods known in the art.

The separation and purification of the *T. litoralis* DNA polymerase contained in the culture supernatant or the cell extract can be performed by the method described above, or by appropriate combinations of known separating and purifying methods. These methods include, for example, methods utilizing solubility such as salt precipitation and solvent precipitation, methods utilizing the difference in molecular weight such as dialysis, ultra-filtration, gel-filtration, and SDS-polyacrylamide gel electrophoresis, methods utilizing a difference in electric charge such as ion-exchange column chromatography, methods utilizing specific affinity such as affinity chromatography, methods utilizing a difference in hydrophobicity such as reverse-phase high performance liquid chromatography and methods utilizing a difference in isoelectric point such as isoelectric focusing electrophoresis.

One preferred method for isolating and purification of the recombinant enzyme is accomplished using the multi-stage process as follows.

First, the cells, if frozen are thawed, suspended in a suitable buffer such as Buffer A (100 mM NaCl, 25 mM Tris pH 7.5, 0.1 mM EDTA, 10% glycerol, 0.05% Triton X-100), lysed and centrifuged. The clarified crude extract is then heated to 75° C. for approximately 30 minutes. The denatured proteins are removed by centrifuation. The supernatant is then passed through a column that has high affinity for proteins that bind to nucleic acids such as Affigel Blue column (Biorad). The nucleic acids present in the supernatant solution and many of proteins pass through the column and are thereby removed by washing the column with several column volumes with low-salt buffer at pH of about 7.0. After washing, the enzyme is eluted with a linear gradient such as 0.1M to 1.5M NaCl Buffer A. The active fractions are pooled, dialyzed and applied to a phosphocellulose column. The column is washed and DNA polymerase activity eluted with a linear gradient of 0.1 to 1.0M NaCl in Buffer B (100M NaCl, 15 mM KPO$_4$, 0.1 mM EDTA, 10% glycerol, 0.05% Triton X-100, pH 6.8). The fractions are collected and BSA is added to each fraction. The fractions with DNA polymerase activity are pooled. The *T. litoralis* DNA polymerase obtained may be further purified using the standard product purification techniques discussed above.

Stabilization and Use of the *T. litoralis* DNA Polymerase

For long-term storage, the thermostable enzyme of the present invention is stored in the following buffer: 0.05M NaCl, 0.01M KPO$_4$ (pH 7.4), 0.1 mM EDTA and 50% glycerol at −20° C.

The *T. litoralis* DNA polymerase of the present invention may be used for any purpose in which such an enzyme is necessary or desirable. For example, in recombinant DNA technology including, second-strand cDNA synthesis in cDNA cloning, and DNA sequencing. See Maniatis, et al., supra.

The *T. litoralis* DNA polymerase of the present invention may be modified chemically or genetically to inactivate the 3'-5' exonuclease function and used for any purpose in which such a modified enzyme is desirable, e.g., DNA sequencing.

For example, genetically modified *T. litoralis* DNA polymerase may be isolated by randomly mutagenizing the *T. litoralis* DNA polymerase gene and then screening for those mutants that have lost exonuclease activity, without loss of polymerase activity. Alternatively, genetically modified *T. litoralis* DNA polymerase is preferably isolated using the site-directed mutagenesis technique described in Kunkel, T. A., *PNAS* (1985) 82:488-492, the disclosure of which is herein incorporated by reference.

In addition, the *T. litoralis* DNA polymerase of the present invention may also be used to amplify DNA, e.g., by the procedure disclosed in U.S. Pat. Nos. 4,683,195, 4,683,202 and 4,800,159.

The following examples are given to illustrate embodiments of the present invention as it is presently preferred to practice. It will be understood that the examples are illustrative, and that the invention is not to be considered as restricted except as indicated in the appended claims.

EXAMPLE I

Purification of a Thermostable DNA Polymerase from *Thermococcus litoralis*

*Thermococcus litoralis* strain NS-C (DSM No. 5473) was grown in the media described by Belkin, et al. supra, containing 10 g/l of elemental sulfur in a 100 liter fermentor at its maximal sustainable temperature of approximately 80° C. for two days. The cells were cooled to room temperature, separated from unused sulfur by decanting and collected by centrifugation and stored at −70° C. The yield of cells was 0.8 g per liter.

183 g of cells obtained as described above, were suspended in 550 ml of buffer A (10 mM $KPO_4$ buffer, pH 7.4; 1.0 mM EDTA, 1.0 mM beta-mercaptoethanol) containing 0.1M NaCl and sonicated for 5 minutes at 4° C. The lysate was centrifuged at 15,000 g for 30 minutes at 4° C. The supernatant solution was passed through a 470 ml Affigel blue column (Biorad). The column was then washed with 1000 ml of buffer A containing 0.1M NaCl. The column was eluted with a 2000 ml linear gradient from 0.1 to 2.0M NaCl in buffer A. The DNA polymerase eluted as a single peak at approximately 1.3M NaCl and represented 80% of the activity applied. The peak activity of DNA polymerase (435 ml) was dialyzed against 4 liters of buffer A, and then applied to 80 ml Phosphocellulose column, , equilibrated with buffer A containing 0.1M NaCl. The column was washed with 160 ml of buffer A containing 0.1M NaCl, and the enzyme activity was eluted with 1000 ml linear gradient of 0.1 to 1.0M NaCl in buffer A. The activity eluted as a single peak at 0.6M NaCl and represented 74% of the activity applied. The pooled activity (150 ml) was dialyzed against 900 ml of buffer A and applied to a 42 ml DNA-cellulose column. The column was washed with 84 ml of buffer A containing 0.1M NaCl, and the enzyme activity eluted with a linear gradient of buffer A from 0.1 to 1.0M NaCl. The DNA polymerase activity eluted as a single peak at 0.3M NaCl, and represented 80% of the activity applied. The activity was pooled (93 ml). The pooled fractions were dialyzed against 2 liters of buffer A containing 0.05M NaCl and then applied to a 1.0 ml HPLC mono-Q column (Pharmacia). The DNA polymerase activity was eluted with a 100 ml linear gradient of 0.05M to 1.0M NaCl in buffer A. The DNA polymerase activity eluted as a single peak at 0.1M NaCl and represented 16% of the activity applied. The pooled fractions (3.0 ml) were diluted to 6 ml with buffer A and applied to an 1.0 ml HPLC mono-S column (Pharmacia) and eluted with a 100 ml linear gradient in buffer A from 0.05 to 1.0M NaCl. The activity eluted as a single peak at 0.19M NaCl and represented 75% of the activity applied.

By SDS-polyacrylamide gel electrophoresis (SDS-PAGE) and subsequent staining of the proteins using a colloidal stain (ISS Problue) more sensitive than Coomassie Blue (Neuhoff, et al., *Electrophoresis* (1988) 9:255-262), it was determined that the DNA polymerase preparation was approximately 50% pure: two major bands were present, one at 90,000 to 95,000 daltons and a doublet at 18,000 daltons. FIG. No. 1A. A very minor band was evident at approximately 80,000 to 85,000 daltons. At this level of purification the polymerase had a specific activity of between 30,000 and 50,000 units of polymerase activity per mg of polymerase protein. On a separate SDS-polyacrylamide gel verification of the identity of the stained band at 90,000 to 95,000 daltons was obtained by cutting the gel lane containing the purified *T. litoralis* polymerase into 18 slices. Embedded proteins were eluted from the gel by crushing the gel slices in a buffer containing 0.1% SDS and 100 μg/ml BSA. The eluted proteins were denatured by exposure to guanidine HCl, then renatured via dilution of the denaturant as described by Hager and Burgess *Analytical Biochemistry* (1980) 109:76-86. Polymerase activity as measured by incorporation of radioactivity labeled $^{32}$P-dCTP into acid-insoluble DNA (as previously described) and assayed for exonuclease activity (as measured by the release of $^3$H-labelled DNA to an acid soluble form as described in Example V). As shown in FIG. No. 1B, only the 90,000 to 95,000 daltons band alone showed either significant polymerase activity or exonuclease activity.

The DNA polymerase preparation was dialyzed against buffer A containing 0.05M NaCl. As was determined by SDS-PAGE, much of the 18,000 dalton protein precipitated out of the solution. The yield of *T. litoralis* DNA polymerase was determined to be 0.5 mg by quantitative protein analysis, and this represented 6.5% of the total activity present in the starting crude extract.

Purified *T. litoralis* polymerase was electrophoresed and stained with either Coomassie Blue or the colloidal stain (ISS Problue) previously described to detect protein. One deeply staining protein band was seen at about 90,000 to 95,000 daltons; this molecular weight determination was obtained by comparison on the same gel to the migration of the following marker proteins (Bethesda Research Laboratories): myosin, 200,000 daltons; phosphorylase B, 97,400 daltons; BSA, 68,000 daltons; ovalbumin, 43,000 daltons, carbonic anhydrase 29,000 daltons; b-lactoglobulin, 18,400 daltons; lysoyzme 14,300 daltons.

EXAMPLE II

Cloning of *T. litoralis* DNA Polymerase Gene

A. PRODUCTION OF MOUSE ANTI-*T. LITORALIS* DNA POLYMERASE ANTISERUM

Immunization of Mice

A 3 ml solution containing 0.4 mg of polymerase protein (obtained by the method of Example I) was concentrated at 4° C. to approximately 0.3 ml and used to inoculate two mice. The purified *T. litoralis* polymerase preparation consisted of four bands of approximately 85-95, 75-85, and a doublet of 10-25 kDal on Coomassie blue stained SDS-PAGE gels. As shown in Example I, the *T. litoralis* polymerase is approximately 90-95 kDal. Both *T. litoralis* polymerase antisera recognize all four proteins present in the immunogen.

The immunization schedule was as follows: mouse one was immunized intraperitoneally (IP) with 20 μg of *T. litoralis* polymerase, prepared as above, in Freunds' complete adjuvant (FCA). Seven days later, both mice were immunized IP with 50 μg *T. litoralis* polymerase in FCA. Twenty-seven days later both mice were immunized IP with 30 μg *T. litoralis* polymerase for mouse one and 50 μg *T. litoralis* polymerase for mouse two in Freunds' incomplete adjuvant. Mouse one was bled two weeks later and mouse two was bled 20 days later. Sera was prepared from blood by standard methods (Harlow and Lane, *Antibodies: A Laboratory Manual*, 1988).

Anti-*T. litoralis* polymerase antisera was diluted in TBSTT (20 mM Tris pH 7.5, 150 mM NaCl, 0.2% Tween 20, and 0.05% Triton-X 100) containing 1% BSA, 0.1% NaAzide, 0.1% PMSF.

Preabsorption of Anti-*T. litoralis* Polymerase Antiserum Against *E. coli* lysates Since most sera react with *E. coli* proteins, *T. litoralis* polymerase antisera were preabsorbed, using the following method, against *E. coli* proteins to reduce background reactivity when screening libraries or recombinant antigens. *E. coli* cell paste was thawed and lysed by sonication and soluble protein was bound to Affigel 10 (Biorad) as described by the manufacturer. 4 ml of *E. coli* resin were washed two times in TBS (TBSTT without detergents). 0.35 ml of sera was diluted approximately 1 to 5 in TBSTT, 1% BSA, 0.1% NaAzide and mixed with resin overnight at 4° C. The resin was pelleted by centrifugation and washed. The recovered preabsorbed sera was at a 1 to 17 dilution and was stored frozen at −20° C. until use.

For screening, preabsorbed sera was diluted as above to a final concentration of 1:200.

B. IDENTIFICATION OF A PROBE FOR THE *T. litoralis* POLYMERASE GENE

Construction of a lambda gt11 Expression Library

A probe for the *T. litoralis* polymerase gene was obtained following immunological screening of a lambda gt11 expression library.

*T. litoralis* DNA was partially digested as follows: four µg of *T. litoralis* DNA was digested at 37° C. with five units of Eco RI in a 40 µl reaction using Eco RI buffer (Eco RI buffer=50 mM NaCl, 100 mM Tris pH 7.5, 20 mM MgCl$_2$, 10 mM BME). Three µl of 100 mM EDTA was added to 15 µl samples at 30, 45 and 60 minutes. 2 µg of *T. litoralis* DNA was digested for 90 minutes at 37° C. with 20 units of Eco RI in 20 µl reaction using Eco RI buffer and the reaction was stopped by adding 2 µl of 100 mM EDTA. 0.2 µg of each digest was electrophoresed on an agarose gel to monitor the extent of digestion. Approximately 3 µg of *T. litoralis* DNA Eco RI partials (14 µl from the 60-minute digest and 19 µl from the 90-minute digest) were pooled to form the "Eco RI pool" and heated at 65° C. for 15 minutes.

0.5 µl of the Eco RI pool were ligated to 0.28 µg of Eco RI cut, bacterial alkaline phosphatase treated lambda gt11 DNA in a five µl reaction using standard ligation buffer (ligation buffer=66 mM Tris pH 7.5, 1 mM ATP, 1 mM spermidine, 10 mM MgCl2, 15 mM DTT, and 2 mg/ml gelatin) and 0.5 µl T4 DNA ligase (New England Biolabs No. 202). The ligation was performed at 16° C. overnight. 4 µl of this ligation reaction were packaged using Gigapack Gold (Stratagene) according to the manufacturers instructions. After incubation at room temperature for two hours, the packaged phage were diluted in 500 µl of SM (SM=100 mM NaCl, 8 mM MgSO$_4$, 50 mM Tris pH 7.5, 0.01% gelatin) plus three drops chloroform. The packaged Eco RI library was called sample V6-1 and consisted of 1.1×10$^5$ individual phage. *E. coli* strain ER1578 was used for phage infection.

Immunological Screening of Lambda gt11 Expression Library

The initial phage library was screened (Young, R. A. and R. W. Davis *Science*, (1983) 222:778–782) with a 1:200 dilution of the antiserum produced above. 36 phage (V10-22 through V10-55) which reacted with the anti-*T. litoralis* DNA polymerase antiserum were picked and 16 phage were plaque purified.

The 16 antibody positive phage were used to lysogenize *E. coli* K-12 strain Y1089. Lysogens were screened for thermostable DNA polymerase activity, no activity was detected.

Western blots (Towbin, et al., *PNAS*, (1979) 76:4350–4354) from these 16 lysates were probed with anti-*T. litoralis* polymerase antiserum. All proteins from these lysates which reacted with *T. litoralis* polymerase antiserum were smaller than *T. litoralis* polymerase, and were also smaller than beta-galactosidase, indicating that none were fusion proteins with beta-galactosidase.

Eight of the 16 antibody positive phage were used to affinity purify epitope-specific antibodies from total antiserum (Beall and Mitchell, *J. Immunological Methods*, (1986) 86:217–223).

The eight affinity purified sera were used to probe Western blots of both purified *T. litoralis* polymerase and *T. litoralis* crude lysates. Antibody purified from NEB 618 plaques specifically reacted with *T. litoralis* polymerase in purified and *T. litoralis* crude lysates. This was strong evidence that phage NEB 618 encodes approximately 38 kDal of the amino terminus of the *T. litoralis* polymerase.

Characterization of Phage NEB 618 and Subcloning of Eco RI Inserts

Western blot analysis indicated that phage NEB 618 synthesized several peptides ranging in size from approximately 15–40 kDal which bound *T. litoralis* polymerase antisera. DNA from phage NEB 618 was purified from liquid culture by standard procedures (Maniatis, et al., supra.) Digestion of NEB 618 DNA with Eco RI yielded fragments of 1.3 and 1.7 kb. An Eco RI digest of NEB 618 DNA was ligated to Eco RI cut pBluescript DNA. 20 µg of pBluescriptSK+ were digested with 40 units of Eco RI in 40 µl Eco RI buffer at 37° C. for three hours, followed by 65° for 15 minutes. 10 µg of NEB 618 DNA were digested with 40 units of Eco RI in 40 µl Eco RI buffer at 37° C. for 75 minutes, followed by 65° C. for 15 minutes. 1.75 µg of Eco RI cut NEB 618 DNA were ligated to 20 ng Eco RI cut pBluescriptSK+ with one µl T4 DNA ligase (New England Biolabs No. 202) in 10 µl ligation buffer. The ligation was performed overnight at 16° C. JM101 CaCl competent cells (Maniatis, et al., supra) were transformed with 5 µl of the ligation mixture. Of 24 recombinants examined, all but one contained the 1.7 kb fragment; clone V27-5.4 contained the 1.3 kb *T. litoralis* DNA fragment.

Antibodies from *T. litoralis* polymerase mouse antisera were affinity purified, as described above, on lysates from V27-5.4 (encoding the 1.3 kb Eco RI fragment) and V27-5.7 (encoding the 1.7 kb Eco RI fragment in pBluescript) and reacted with Western blot strips containing either purified or crude *T. litoralis* polymerase. Antibodies selected on lysates of V27-5.4 reacted with *T. litoralis* polymerase in both crude and purified preparations. In addition, the first three amino acids from the N-terminal protein sequence of native *T. litoralis* polymerase (methionine-isoleucine-leucine) are the same as in the predicted open reading frame (ORF) in the V27-5.4 clone.

From these results it was concluded that V27-5.4 encoded the amino terminal of *T. litoralis* polymerase. The 1.3 kb Eco RI fragment of V27-5.4 comprises nucleotides 1 to 1274 of FIG. No. 6. The insert DNA was large enough to encode the biggest peptides synthesized by this clone, but not the entire *T. litoralis* polymerase.

C. CONSTRUCTION AND SCREENING OF *T. litoralis* SECONDARY LIBRARIES

Antibody screening discussed above, had identified the DNA fragment coding the amino terminal half of the *T. litoralis* polymerase. In order to find a fragment large enough to code for the entire gene, restriction digests of *T. litoralis* DNA were probed with the amino terminal half of the polymerase gene contained in clone V27-5.4. Restriction digests were performed in separate tubes using a master mix which contained 1.2 µg of *T. litoralis* DNA in 39 µl of restriction enzyme buffer (REB, restriction enzyme buffer=50 mM NaCl, 10 mM Tris pH 7.5, 20 mM MgCl2, 10 mM BME), to which 1.5-200 U of enzyme were added as followed: 1.5 U AvrII, 9 U EaeI, 10 U NheI, 20 U NotI, 9 U SpeI, 20 U XhoI, 30 U XbaI, 20 U SacI, 10 U BamHI, 20 U ClaI, 20 U HindIII, 20 U PstI, 12 U NaeI, 10 U ScaI, 12 U XmnI, 20 U EcoRV, 20 U Sal, 20 U Eco RI, 200 U EagI, 20 U DraI, 5 U HapI, 8 U NruI, 4 U SnaBI, 8 U StuI, 10 U BclI, 8 U BglII, 10 U RsaI, 10 U HaeIII, 8 U AluI, 4 U HincII, 10 U PvuII, 6 U SspI. One µl 10 mg/ml BSA was added to the HincII digest. BalI digest was prepared as above except there was 0 mM NaCl in the buffer. All digests were overnight at 37° C. except BclI which was incubated at 50° C. Digests were electrophoresed on agarose gels and transferred to NC (Southern, *J. Mol. Biol.* (1975) 98:503-517). The filters were probed with radiolabeled V27-5.4 DNA and hybridization was detected by autoradiography. In most digests, V27-5.4 DNA hybridized to fragments greater than 20 kb, except BamHI (approximately 14 kb), Eco RI (1.3 kb), HindIII (approximately 2.4, 5.4 kb), XbaI (approximately 8 kb), ClaI (approximately 4.4, 5.5 kb), BalI (approximately 8.5 kb), HincII (approximately 2.1, approximately 2.4 kb), NruI (approximately 5.5 kb), BglII (approximately 2.9 kb), HaeIII (approximately 1.3, approximately 1.4 kb) and RsaI Which gave numerous small bands.

Digests yielding single fragments large enough to encode the entire polymerase gene, estimated to be 2.4-3 kb, based on the size of the native protein, were BamHI, XbaI, and NruI.

BamHI Library

A BamHI genomic library was constructed using lambda DashII. Lambda DashII is a BamHI substitution vector that can be used to clone 10-20 kb BamHI DNA fragments. 25-75 nanograms of *T. litoralis* genomic DNA digested with BamHI, as described above, was ligated to 0.5 µg BamHI digested, calf intestine phosphatase treated lambda DashII DNA in five µl of standard ligation buffer including 0.5 µl T4 DNA ligase (New England Biolabs No. 202). Three µl of the ligation reaction was packaged (Gigapack Plus, Stratagene) as described above. Plaque lifts of 8,000 plaques from the lambda DashII library were probed with labeled gel purified 1.3 kb Eco RI fragment from clone V27-5.4 (Maniatis, et al., supra). 2.5% of the phage hybridized to the 1.3 kb Eco RI DNA fragment, two of which were plaque purified (clones lambda NEB 619 and lambda V56-9). Both phage contained a 12-15 kb BamHI fragment which hybridized to the 1.3 kb Eco RI fragment and contained the approximately 8 kb XbaI and approximately 5.5 kb NruI fragments. The BamHI insert was subcloned into pBR322. Colonies containing this fragment grew very poorly and, based on the polymerase assay described above, failed to produce detectable levels of thermostable DNA polymerase.

XbaI Library

*T. litoralis* DNA digested with XbaI was cloned into the XbaI site of pUC19. Colony lifts were probed with radiolabeled V27-5.4 DNA. No positive clones were detected.

The XbaI fragment from the BamHI insert in lambda NEB 619 (BamHI library above) was subcloned into the XbaI site of pUC19. Approximately 0.3 µg of NEB 619 DNA digested with BamHI was ligated to 0.1 µg pUC19 DNA digested with BamHI using two µl T4 DNA ligase (New England Biolabs No. 202) in 20 µl of standard ligation buffer. The ligation was incubated overnight at 16° C. CaCl competent JM101 and XL-1 cells were transformed with five µl of ligation mix and incubated overnight at 37° C. (Maniatis, et al., supra). Colony lifts were probed with radiolabeled purified 1.3 kb Eco RI fragment from V27-5.4 DNA. No positives were detected. Competent RRI cells were transformed with 10 µl of ligation mix and incubated overnight at 30° C. Micro-colonies were picked and mini-plasmid preparations (boiling method, Maniatis, et al., supra) analyzed. Most of these clones contained the approximately 8 kb XbaI fragment. The rationale for this latter experiment was that since the BamHI clones grew poorly, there would be an increased chance of isolating a plasmid containing the *T. litoralis* polymerase gene from an XbaI colony that also grew slowly. Also, lower temperature of incubation results in less copies of pUC19 plasmids per cell. These results provided evidence that the *T. litoralis* polymerase gene was toxic to *E. coli*. Using the polymerase activity assay described above, no thermostable polymerase activity was detected in these clones. Restriction analysis indicated that the XbaI clones should contain the entire polymerase gene. See FIG. No. 2.

NruI Libraries

Approximately 0.3 µg of NEB 619 DNA (BamHI library above) cut with NruI was ligated to 0.1 µg of pUC19 DNA cut with HincII exactly as described for the XbaI library. Again, no positives were found by hybridization when cells were incubated at 37° C., but when transformants were incubated at 30° C., many micro-colonies were observed. The majority of these micro-colonies contained the approximately 5.5 kb NruI insert. Using the polymerase activity assay described above, no thermostable polymerase activity was detected in these colonies. Analysis of these colonies determined that when the direction of *T. litoralis* polymerase transcription was the same as lacZ in pUC19, the colonies failed to grow at 37° C. and were extremely unstable. However, colonies in which the direction of *T. litoralis* polymerase transcription was opposite of lacZ in pUC19, such as in clone Nru21, were more stable. This indicated that transcription of *T. litoralis* polymerase is detrimental to *E. coli*, and may explain why it was so difficult to clone the entire gene. Restriction mapping analysis indicated that the NruI clones should contain the entire polymerase gene. See FIG. No. 2.

Conclusions Concerning Direct Cloning of the Polymerase

The *T. litoralis* is approximately 90–95 kDal which would require approximately 2.4–3.0 kb DNA to encode the entire gene. Restriction mapping analysis of the 1.3 kb Eco RI fragment, coding for the amino-terminus of the *T. litoralis* polymerase gene, found within the BamHI, XbaI and NruI clones, discussed above, indicates that all three clones contain the entire polymerase gene. All of these larger clones were unstable in *E. coli*. Therefore, alternate methods, as discussed below, for cloning the polymerase were tested.

D. CLONING THE SECOND HALF OF *T. litoralis* POLYMERASE GENE

It is believed that when the entire *T. litoralis* polymerase gene was cloned in *E. coli* while under its endogenous control, mutations in the gene arose. To prevent selection of inactive mutants, the polymerase gene was cloned from the *T. litoralis* genome in 2 or more pieces which should each separably be inactive and therefore not selected against. Restriction mapping of the *T. litoralis* genome was used to determine which restriction enzymes would produce fragments that would be appropriate for cloning the second half of the *T. litoralis* polymerase gene. Although the above data indicates that expression of *T. litoralis* polymerase was toxic for *E. coli*, it was also possible that DNA sequences themselves, in or outside of the coding region, were toxic. Therefore, the minimum sized fragment which could encode the entire gene was determined to be the best choice. Restriction analysis indicated that there was an approximately 1.6 kb Eco RI fragment adjacent to the 3' end of the amino terminal 1.3 kb Eco RI fragment (see FIG. No. 2) which could possibly complete the polymerase gene.

Hybridization Probe for the Second Half of the *T. litoralis* DNA Polymerase Gene Since none of the previous clones expressed thermostable polymerase activity, it was possible that they had accumulated mutations in the coding sequence and would therefore not be suitable sources of the second half of the gene. Hybridization probes were therefore required in order to clone the downstream fragments from the genome. The approximately 3.2 kb NdeI/ClaI fragment from clone Nru21 (the Nru21 clone contains an approximately 5.5 kb insert, beginning approximately 300 bp upstream from the start of the polymerase gene) was subcloned into pSP73 (Promega) creating clone NC11. CaCl competent RRI cells were transformed, as above, with the ligation mixture. Mini-plasmid preps of transformants were analyzed by digestion with NdeI and ClaI and clone NC11 containing the *T. litoralis* 3.2 kb NdeI/ClaI fragment was identified. This clone was stable in *E. coli*. The pNC11 insert was sequenced (Sanger, et al., *PNAS*, (1977) 74:5463–5467). The ClaI end was identical to the V27-5.4 sequence (1.3 kb Eco RI fragment coding for the amino-terminus of the *T. litoralis* polymerase). The 1.3 kb Eco RI junction and beyond was sequenced using primers derived from the 1.3 kb Eco RI fragment sequence. The NdeI end was sequenced from primers within the vector.

Screening of Eco RI Genomic Libraries

10 μg of NC11 were digested with 30 U of Eco RI in 100 μl of Eco RI buffer at 37° C. for two hours. The approximately 1.6 kb Eco RI fragment was purified on DE-81 paper (Whatman) after electrophoresis. The approximately 1.6 kb Eco RI fragment was radiolabeled and used to probe the original Eco RI lambda gtll library. Infection and plaque lifts were performed as above. Three positives were identified and plaque purified. All contain the approximately 1.6 kb Eco RI fragment, but some also contain other inserts.

An Eco RI library was also constructed in lambda ZapII. 2 μg of *T. litoralis* DNA were digested with 20 U Eco RI for five hours at 37° C. in 20 μl Eco RI buffer and then heat treated at 65° C. for 15 minutes. Approximately 15 nanograms of *T. litoralis* DNA/Eco RI was ligated to 0.5 μg of Eco RI cut, phosphatased lambda ZapII DNA (Stratagene) with 0.5 μl T4 DNA ligase (New England Biolabs No. 202) in 5 μl of ligation buffer at 16° C. overnight. 4 μl of ligated DNA was packaged (GigaPack Gold, Stratagene). Infection and plaque lifts were performed as above. Approximately 1,500 phage were probed with radiolabeled approximately 1.6 kb Eco RI fragment as above. Five hybridization positive plaques were picked and three were plaque purified. Two phage (NEB 620 and V109-2) were rescued as pBluescript recombinants (VI17-1 and V117-2) by in vivo excision according to the manufacturer's instructions (Stratagene). Both contained the approximately 1.6 kb Eco RI fragment plus different second fragments. The 5, end was sequenced and corresponds to the sequence determined from NC11 (ClaI/NdeI fragment). See FIG. No. 2. This Eco RI fragment contains 3/6 of the T4 DNA polymerase family homology islands as described by Wang, et al., supra. The 1.6 kb Eco RI fragment comprises nucleotides 1269 to 2856 of FIG. No. 6.

The sequence of the 1.6 kb Eco RI and ClaI/NdeI fragments indicated that the 1.9 kb Eco RI fragment may be necessary to complete the polymerase gene. Lambda ZapII phage, V110-1 through V110-7, containing the 1.9 kb Eco RI fragment were identified as described above for NEB 620 using labeled probes. Two phage (VI10-2 and V110-4) were rescued as pBluescript recombinants (V153-2 and V153-4) by in vivo excision according to the manufacturers instructions (Stratagene). Both contained the approximately 1.9 kb Eco RI fragment plus different second fragments. The 1.9 kb Eco RI fragment had sequence identity with the overlappying region in Nc11. The 1.9 kb Eco RI fragment comprises nucleotides 2851 to 4771 of FIG. No. 6.

The entire *T. litoralis* polymerase gene has been cloned as BamHI, XbaI and NruI fragments which were unstable and from which the active enzyme was not detected. The gene has also been cloned in four pieces (1.3 kb Eco RI fragment, approximately 1.6 kb Eco RI fragment, approximately 1.9 kb Eco RI fragment and an Eco RI/BamHI fragment containing the stop codon). The 1.3 kb Eco RI fragment stably expresses the amino terminal portion of the polymerase.

EXAMPLE III

Cloning of Active *T. litoralis* DNA Polymerase

The *T. litoralis* polymerase gene found on the 14 kb BamHI restriction fragment of bacteriophage NEB619 (ATCC No. 40795), was sequenced using the method of Sanger, et al., *PNAS* (1977) 74:5463–5467. 5837 bp of continuous DNA sequence (SEQ ID NO:1) was determined beginning from the 5, end of the 1.3 kb EcoRI fragment (position NT 1), see FIG. No. 6.

From analysis of the DNA sequence, it was determined that the polymerase gene begins at NT 291 in the 1.3 kb EcoRI fragment. A translation termination site beginning at NT 5397 was also located. Since the apparent molecular weight of *T. litoralis* polymerase was approximately 90–95 Kdal, it was predicted that the gene should be ~2900 bp. Instead, a 5106 bp open reading frame (ORF) was identified with a coding capacity of 1702 amino acids (aa) or ~185 Kdal.

By sequence homology with other DNA polymerases, an example of which is set out in FIG. No. 7, it was discovered that the *T. litoralis* polymerase gene was interrupted by an intron or intervening sequence in DNA polymerase consensus homology region III (Wang, T., et al., *FASEB Journal* (1989) 3:14–21 the disclosure of which is herein incorporated by reference). The conserved amino acids of the consensus DNA polymerase homology region III are shown in FIG. No. 7. In the Figure, the conserved amino acids are underlined. As can be seen in FIG. No. 7, the left side of the *T. litoralis* homology island III (SEQ ID NO:2) begins at NT 1737, and homology to the consensus sequence is lost after the Asn and Ser residues. The right side of the *T. litoralis* homology island III (SEQ ID NO:3) can be picked up at NT 3384, at the Asn and Ser residues. When the two *T. litoralis* polymerase amino acid sequences were positioned so that the Asn and Ser residues overlap, as in FIG. No. 7, it was evident that a good match to the DNA polymerase homology region III existed.

Using the homology data, it was therefore predicted that an intervening sequence existed in the *T. litoralis* DNA separating the left and right halves of the DNA polymerase homology region III.

In one preferred embodiment, the intervening sequence was deleted by identifying unique restriction enzyme sites in the coding region which were near the intervening sequence splice junction. A synthetic duplex oligonucleotide was synthesized, and used to bridge the gap between the two restriction fragments. A multi-part sequential ligation of the carboxy end restriction fragments, the bridging oligonucleotide, the amino end restriction fragment, and the expression vector, resulted in the formation of an expression vector containing an intact polymerase gene with the intervening sequence deleted.

Specifically, the DNA fragments or sequences used to construct the expression vector of the present invention containing the *T. litoralis* DNA polymerase gene with the intervening sequence deleted were as follows:

1. An NdeI site was created by oligonucleotide directed mutagenesis (Kunkel, et al., *Methods in Enzymology* (1987) 154:367:382) in plasmid V27-5.4 (Example II, Part B) such that the initiation codon of the polymerase coding region is contained within the NdeI site.

| | |
|---|---|
| Original sequence (nucleotides 288–293) | ... TTT ATG ... |
| New sequence | ... CAT ATG ... |

Sequences from newly created NdeI site to the ClaI site (approximately 528 base pairs) were utilized in the construction of the expression vector.

2. An approximately 899 bp sequence between the ClaI and PvuI site of NC11 (Example II, Part D).

3. A synthetic duplex which spans the intervening sequence, connecting PvuI and Bsu36I sites derived from other fragments, as set out in FIG. No. 12.

In FIG No. 12, the first line indicates the original sequence at the 5' end of the splice junction (nucleotides 1721–1784, SEQ ID NO:1), the second line indicates the original sequence of the 3' end of the splice junction (nucleotides 3375–3415, SEQ ID NO:1), and the third (SEQ ID NO: 4) and fourth (SEQ ID NO:5) lines indicate the sequence of the synthetic duplex oligonucleotide.

4. A Bsu36I to BamHI fragment, approximately 2500 base pairs, derived from bacteriophage NEB 619 (Example II, Part C).

5. A BamHI to NdeI fragment of approximately 6200 base pairs representing the vector backbone, derived from pET11c (Studier, *Methods in Enzymology*, (1990) 185:66–89), and which includes:

a) The T7 phi 10 promoter and ribosome binding site for the gene 10 protein
b) Ampicillin resistance gene
c) lacI$^q$ gene
d) Plasmid origin of replication
e) A four-fold repeat of the ribosomal transcription terminators (rrnb), Simons, et al., *Gene* (1987) 53:85–96.

The above DNA fragments, 1–5, were sequentially ligated under appropriate conditions using T4 DNA ligase. The correct construct was identified by restriction analysis and named pPR969. See FIG. No. 8. pPR969 was used to transform *E. coli* strain RRI, creating a strain designated NEB 687. A sample of NEB 687 was deposited with the American Type Culture Collection on Dec. 7, 1990 and bears ATCC No. 68487.

In another preferred embodiment, the *T. litoralis* polymerase gene, with the intervening sequence deleted, was cloned into a derivative of the Studier T7 RNA polymerase expression vector pETIlc (Studier, (1990) supra). The recombinant plasmid V174-1B1 was used to transform *E. coli* strain BL21(DE3)pLysS, creating strain 175-1B1, designated NEB671. See FIG. Nos. 5 and 10.

A sample of NEB671 was deposited with the American Type Culture Collection on Oct. 17, 1990 and bears ATCC No. 68447.

A comparison between the predicted and observed molecular weights of the polymerase, even with the intervening sequence deleted, revealed a discrepancy. The predicted molecular weight of the polymerase after removal of the intervening sequence in region III is 132-kb, while the observed molecular weight of either the native (see Example I) or recombinant (see Example IV) polymerase is 95-kb. While not wishing to be bound by theory, it is believed that the molecular weight discrepancy is due to an intron between homology regions I and III. This finding is based on the following observations: The distance between homology regions III and I varies from 15–135 amino acids in members of the pol alpha family (Wang, (1989) supra). In *T. litoralis* there are 407 amino acids or ~44-kD separating these regions. *T. litoralis* DNA polymerase is very similar to human pol alpha except for 360 amino acids between conserved homology regions I and III where no similarity exists.

In addition, as determined by PAGE, a thermostable endonuclease of approximately 35-kD is also produced by the *T. litoralis* DNA polymerase clones of the present invention (see Example X). This endonuclease was purified to homogeneity by standard ion exchange chromatography, and was sequenced at its amino-terminal. The first 30 amino acids of the endonuclease correspond to the amino acids encoded beginning at nucleotide 3534 of the polymerase clone (SEQ ID NO:1). This corresponds to the portion of the polymerase which lacks homology with other known polymerases. This endonuclease does not react with anti-*T. litoralis* DNA polymerase antisera. While the exact mechanism by which the endonuclease is spliced out of the polymerase is unknown, it occurs spontaneously in both *E. coli* and *T. litoralis*.

EXAMPLE IV

Purification of Recombinant *T. litoralis* DNA Polymerase

*E. coli* NEB671 (ATCC No. 68447) was grown in a 100 liter fermentor in media containing 10 g/liter tryptone, 5 g/liter yeast extract, 5 g/liter NaCl and 100 mg/liter ampicillin at 35° C. and induced with 0.3 mM IPTG at midexponential growth phase and incubated an additional 4 hours. The cells were harvested by centrifugation and stored at $-70°$ C.

580 grams of cells were thawed and suspended in Buffer A (100 mM NaCl, 25 mM $KPO_4$ at pH 7.0, 0.1 mM EDTA, 0.05% Triton X-100 and 10% glycerol) to a total volume of 2400 ml. The cells were lysed by passage through a Gaulin homogenizer. The crude extract was clarified by centrifugation. The clarified crude extract volume was adjusted to 2200 mls with the above buffer and was heated to 75° C. for 30 minutes. The particulate material was removed by centrifugation and the remaining supernatant contained about 3120 mg of soluble protein.

The supernatant was applied to a DEAE-sepharose column (5×13 cm; 255 ml bed volume) linked in series to a phosphocellulose column (5×11 cm; 216 ml bed volume). The DEAE-sepharose flow-through fraction, containing the bulk of the enzyme, passed immediately onto the phosphocellulose column. Both columns were washed with 300 mls Buffer A, the two columns were disconnected, and the protein on the phosphocellulose column was eluted with a 2 liter linear gradient of NaCl from 0.1M to 1M formed in Buffer A.

The column fractions were assayed for DNA polymerase activity. Briefly, 1–4 μl of fractions were incubated for 5–10 minutes at 75° C. in 50 μl of 1X *T. litoralis* DNA polymerase buffer (10 mM KCl, 20 mM Tris-HCl (ph 8.8 at 24° C.), 10 mM $(NH_4)_2SO_4$, 2 mM $MgSO_4$ and 0.1% Triton X-100) containing 30 μM each dNTP and $^3$H-labeled TTP, 0.2 mg/ml activated calf thymus DNA and 100 μg/ml acetylated BSA. The mixtures were applied to Whatman 3 mm filters and the filters were subjected to three washes of 10% TCA followed by two washes of cold ethanol. After drying of the filters, bound radioactivity representing incorporation of $^3$H-TTP into the DNA was measured. The active fractions were pooled and the enzyme activity levels in each pool were assessed using the above assay conditions except the dNTP level was raised to 200 μM each dNTP. Under these conditions one unit of enzyme activity was defined as the amount of enzyme that will incorporate 10 nmoles of dNTP into acid-insoluble material at 75° C. in 30 minutes.

The active fractions comprising a 300 ml volume containing 66 mg protein, were applied to a hydroxylapatite column (2.5×5 cm; 25 ml bed volume) equilibrated with Buffer B (400 mM NaCl, 10 mM $KPO_4$ at pH 7.0, 0.1 mM EDTA, 0.05% Triton X-100 and 10% glycerol). The protein was eluted with a 250 ml linear gradient of $KPO_4$ from 10 mM to 500 mM formed in Buffer B. The active fractions, comprising a 59 ml volume containing 27 mg protein, was pooled and dialyzed against Buffer C (200 mM NaCl, 10 mM Tris-HCl at pH 7.5, 0.1 mM EDTA, 0.05% Triton X-100 and 10% glycerol).

The dialysate was applied to a heparin-sepharose column (1.4×4 cm; 6 ml bed volume) and washed with 20 ml Buffer C. A 100 ml linear gradient of NaCl from 200 mM to 700 mM formed in Buffer C was applied to the column. The active fractions, comprising a 40 ml volume containing 16 mg protein was pooled and dialyzed against Buffer C.

The dialysate was applied to an Affi-gel Blue chromatography column (1.4×4 cm; 6 ml bed volume), washed with 20 mls Buffer C, and the protein was eluted with a 95 ml linear gradient from 0.2M to 2M NaCl formed in Buffer C. The active fractions, comprising a 30 ml volume containing 11 mg of protein, was dialyzed against a storage buffer containing 200 mM KCl, 10 mM Tris-HCl (pH 7.4), 1 mM DTT, 0.1 mM EDTA, 0.1% Triton X-100, 100 μg/ml BSA and 50% glycerol.

The *T. litoralis* DNA polymerase obtained above had a specific activity of 20,000–40,000 units/mg.

Characterization of Recombinant *T. litoralis* Polymerase

Recombinant and native *T. litoralis* polymerase had the same apparent molecular weight when electrophoresed in 5–10% SDS-PAGE gradient gels. Recombinant *T. litoralis* polymerase maintains the heat stability of the native enzyme. Recombinant *T. litoralis* polymerase has the same 3'→5' exonuclease activity as native *T. litoralis* polymerase, which is also sensitive to inhibition by dNTPs.

EXAMPLE V

Over-Expression of the *Thermococcus litoralis* DNA Polymerase Gene

The *T. litoralis* DNA polymerase gene, with the intron deleted, e.g., V174-1B1 obtained in Example III, may be used in a number of approaches, or combinations thereof, to obtain maximum expression of the cloned *T. litoralis* DNA polymerase.

One such approach comprises separating the *T. litoralis* DNA polymerase gene from its endogenous control elements and then operably linking the polymerase gene to a very tightly controlled promoter such as a T7 expression vector (Rosenberg, et al., *Gene* (1987) 56:125–135). Insertion of the strong promoter may be accomplished by identifying convenient restriction targets near both ends of the *T. litoralis* DNA polymerase gene and compatible restriction targets on the vector near the promoter, or generating restriction targets using site directed mutagenesis (Kunkel, (1984), supra), and transferring the *T. litoralis* DNA polymerase gene into the vector in such an orientation as to be under transcriptional and translational control of the strong promoter.

*T. litoralis* DNA polymerase may also be overexpressed by utilizing a strong ribosome binding site placed upstream of the *T. litoralis* DNA polymerase gene to increase expression of the gene. See, Shine and Dalgarno, *Proc. Natl. Acad. Sci. USA* (1974) 71:1342–1346, which is hereby incorporated by reference.

Another approach for increasing expression of the *T. litoralis* DNA polymerase gene comprises altering the DNA sequence of the gene by site directed mutagenesis or resynthesis to contain initiation codons that are more efficiently utilized than *E. coli*.

Finally, *T. litoralis* DNA polymerase may be more stable in eukaryote systems like yeast and Baculovirus.

The *T. litoralis* DNA polymerase may be produced from clones carrying the *T. litoralis* DNA polymerase gene by propagation in a fermentor in a rich medium containing appropriate antibiotics. Cells are thereafter harvested by centrifugation and disrupted by sonication to produce a crude cell extract containing the *T. litoralis* DNA polymerase activity.

The crude extract containing the *T. litoralis* DNA polymerase activity is purified by the method described in Example I, or by standard product purification techniques such as affinity-chromatography, or ion-exchange chromatography.

EXAMPLE VI

Production of a *T. litoralis* DNA Polymerase 3' to 5' Exonuclease Mutant

A *T. litoralis* DNA polymerase lacking 3' to 5' exonuclease activity was constructed using site-directed mutagenesis to alter the codons for asp141 and glu143 to code for alanine. Site-directed mutagenesis has been used to create DNA polymerase variants which are reported to have reduced exonuclease activity, including phi29 (*Cell* (1989) 59:219-228 ) DNA polymerase I (*Science* (1988) 240:199-201) and T7 DNA polymerases (U.S. Pat. No. 4,942,130).

Site-directed mutagenesis of the polymerase of the present invention was accomplished using a modification of the technique described by Kunkel, T. A., *PNAS* (1985) 82:488–492, the disclosure of which is herein incorporated by reference. The V27-5.4 plasmid (see Example 2, Part B) was used to construct the site-directed mutants. V27-5.4 encodes the 1.3 kb EcoRI fragment in pBluescript SK+. *E. coli* strain CJ236 (Kunkel, et al., *Methods in Enzymology* (1987) 154:367–382), a strain that incorporates deoxyuracil in place of deoxythymidine, containing the V27-5.4 plasmid was superinfected with the f1 helper phage IR1 (*Virology*, (1982) 122:222–226) to produce single stranded versions of the plasmid.

Briefly, the site-directed mutants were constructed using the following approach. First, a mutant oligonucleotide primer, 35 bases in length, was synthesized using standard procedures. The oligonucleotide was hybridized to the single-stranded template. After hybridization the oligonucleotide was extended using T4 DNA polymerase. The resulting double-stranded DNA was converted to a closed circular dsDNA by treatment with T4 DNA ligase. Plasmids containing the sought after mutations were identified by virtue of the creation of a PvuI site overlapping the changed bases, as set out below. One such plasmid was identified and named pAJG2.

The original and revised sequences for amino acid residues are 141, 142, and 143:

| Original: | .. asp ile glu |
|---|---|
| | .. GAT ATT GAA |
| Altered: | .. ala ile ala |
| | .. GCG ATC GCA |

The newly created PvuI site, used to screen for the alteration, is underlined. Note that the middle codon was changed but that the amino acid encoded by this new codon is the same as the previous one.

An approximately 120 bp ClaI to NcoI fragment from V174-1B1 (see Example III) was replaced by the corresponding fragment bearing the above substitutions from pAJG2, creating pCAS4 (see FIG. No. 9). pCAS4 thus differs from V174-1BI by 4 base pairs, namely those described above.

*E. coli* BL21 (DE3)plysS (*Methods in Enzymology*, (1990) 185:60–89) was transformed with pCAS4, creating strain NEB681. Expression of the mutant *T. litoralis* polymerase was induced by addition of IPTG.

A sample of NEB681 has been deposited with the American Type Culture Collection on Nov. 8, 1990, and bears ATCC No. 68473.

Relative exonuclease activities in the native *T. litoralis* DNA polymerase and the exonuclease minus variant isolated from *E. coli* NEB681 was determined using a uniformly [$^3$H] labeled *E. coli* DNA substrate. Wild type *T. litoralis* DNA polyermase was from a highly purified lot currently sold by New England Biolabs, Inc. The exonuclease minus variant was partially purified through DEAE sepharaose and phosphocellulose columns to remove contaminants which interfered with the exonuclease assays. The indicated number of units of polyermase were added to a 0.1 ml reaction containing *T. litoralis* DNA polymerase buffer [20 mM Tris-Hcl (pH8.8 at 25° C.), 10 mM KCl, 10 mM (NH$_4$)$_2$SO$_4$, 5 mM MgSO$_4$, 0.1% Triton X-100], 0.1 mg/ml bovine serum albumin, and 3 µg/ml DNA substrate (specific activity 200,000 cpum/µg) and the reaction was overlaid with mineral oil to prevent evaporation of the reaction. Identical reactions contained in addition 20 µM dNTP, previously shown to inhibit the exonuclease activity of the wild type enzyme. The complete reaction mixture was incubated at 70° C. for 60 minutes, following which 0.08 ml was removed and mixed with 0.02 ml 0.5 mg/ml sonicated herring sperm DNA (to aid in precipitation of intact DNA) and 0.2 ml of 10% trichloroacetic acid at 4° C. After mixing, the reaction was incubated on ice for 5 minutes, and the DNA then pelleted at 4° C. for 5 minutes in an Eppendorf centrifuge. 0.25 ml of supernatant was mixed with scintillation fluid and counted. The results of the sample counting, corrected for background, are shown in FIG. No. 11.

As illustrated in FIG. No. 11, the exonuclease minus variant was substantially free of exonuclease activity in the presence or absence of dNTPs under conditions where the native polymerase clearly demonstrated exonuclease activity. Conservatively estimating that a level of activity two-fold above background could have been detected, this implies that the exonuclease activity is decreased at least 60-fold in this variant.

EXAMPLE VII

*T. litoralis* DNA Polymerase Half-Life Determination

The thermostability or half-life of the *T. litoralis* DNA polymerase purified as described above in Example 1 was determined by the following method. Purified *T. litoralis* DNA polymerase (25 units) was preincubated at 100° C. in the following buffer: 70 mM tris- HCl (pH 8.8 at 25° C.), 17 mM ammonium sulfate, 7 mM MgCl$_2$, 10 mM beta-mercaptoethanol, 200 μM each

*litoralis* DNA polymerase showed the reverse, an inhibitory response to the presence of deoxynucleotides.

TABLE 1

| Experiment # | Amount | Type of DNA Polymerase | Acid-Soluble CPM (Exonuclease Activities)* | | |
|---|---|---|---|---|---|
| | | | no dNTPS | 30 uM dNTPS | Effect Upon Adding NTPS |
| 1 | 2.5 units | Taq Polymerase | 241 | 1936 | 8 × increase |
| | 3 units | T4 Polymerase | *47608 | 6663 | 7 × decrease |
| | 10 units | Klenow Fragment of *E. coli* Pol. I | 11272 | 2845 | 4 × decrease |
| 2 | 5 units | Taq Polymerase | 338 | 2539 | 8 × increase |
| | 5 units | T4 Polymerase | *46001 | 10418 | >4 × decrease |
| | 5 units | Klenow Fragment of *E. coli* Pol. I | 8757 | 408 | 22 × decrease |
| | 5 units | *T. litoralis* Polymerase | 8573 | 795 | 11 × decrease |

*Nonlinear range of assay deoxynucleotide and 200 μg/ml DNAse-treated DNA. An initial sample was taken at time zero and a small aliquot equivalent to 5% of the enzyme mixture was removed at 10, 20, 40, 60, 90, 120, 150, and 180 minutes. The polymerase activity was measured by determining incorporation of deoxynucleotide into DNA as described previously.

A sample of Taq DNA polymerase obtained from New England Biolabs was subjected to the above assay. An initial sample was taken at time zero and a small aliquot equivalent to 5% of the enzyme mixture was removed at 4, 7, and 10 minutes. As shown in the FIG. No. 3, the half-life of the *T. litoralis* DNA polymerase at 100° C. was 60 minutes, while the half-life of the Taq polymerase at 100° C. was 4.5 minutes.

As shown in FIG. No. 3, the half-life of *T. litoralis* DNA polymerase at 100° C. in the absence of stabilizers was 60 minutes, while in the presence of the stabilizers TRITON X-100 (0.15%) or BSA (100 μg/ml) the half-life was 95 minutes. This was in stark contrast to the half-life of Taq DNA polymerases at 100° C., which in the presence or absence of stabilizers was 4.5 minutes (FIG. No. 3).

EXAMPLE VIII

Determination of 3'-5' Proofreading Activity

I. Response of *T. litoralis* DNA Polymerase to the Absence or Presence of Deoxynucleotides The levels of exonuclease activities associated with polymerases show very different responses to deoxynucleotides. Nonproofreading 5'-3' exonucleases are stimulated tenfold or greater by concomitant polymerization afforded by the presence of deoxynucleotides, while proofreading 3'-5' exonucleases are inhibited completely by concomitant polymerization. Lehman, I. R. *ARB* (1967) 36:645.

The *T. litoralis* DNA polymerase or polymerases with well-characterized exonuclease functions (T4 Polymerase, Klenow fragment) were incubated with 1 μg $^3$H-thymidine-labeled double-stranded DNA (10$^5$ CPM/μg) in polymerization buffer (70 mM tris (pH 8.8 at 24° C.), 2 mM MgCl$_2$, 0.1% Triton and 100 μg/ml bovine serum albumin). After an incubation period of three hours (experiment 1) or four hours (experiment 2) at either 70° C. (thermophilic polymerases) or 37° C. (mesophilic polymerases), the exonuclease-hydrolyzed bases were quantified by measuring the acid-soluble radioactively-labeled bases.

As shown in Table 1, the Taq DNA polymerase, with its 5'-3' exonuclease activity, shows stimulation of exonuclease activity when deoxynucleotides were present at 30 uM. However, polymerases with 3'-5' proofreading exonuclease activities, such as the T4 polymerase, Klenow fragment of *E. coli* polymerase I, or the *T.*

The similarity of responses to the presence or absence of deoxynucleotides of the *T. litoralis* DNA polymerase and the well-characterized Klenow fragment of the *E. coli* DNA polymerase is further shown in FIG. No. 4. Twenty units of either polymerase was incubated with 9 μg $^3$H-thymidine-labeled double-stranded DNA (10$^5$ CPM/μg) in 350 μl polymerization buffer as described above in the presence, or absence of, 30 μM deoxynucleotides. At each time point, 50 μl was removed and the level of acid-soluble radioactively-labeled bases were measured. As FIG. No. 4 documents, the behavior of *T. litoralis* DNA polymerase and the Klenow fragment of *E. coli* DNA polymerase, which contains a well-characterized 3'-5' proofreading exonuclease activity, are very similar.

2. Response of *T. litoralis* DNA Polymerase to Increasing Deoxynucleotide Concentrations Exonuclease activities of polymerases are affected by the level of deoxynucleotides present during polymerization, in as much as these levels affect polymerization. As deoxynucleotide levels are increased towards the Km (Michaelis constant) of the enzyme, the rate of polymerization is increased. For exonuclease functions of polymerases sensitive to the rate of polymerization, changes in exonuclease activity are parallel with increases in deoxynucleotide concentrations. The increase in polymerization rate drastically decreases proofreading 3'-5' exonuclease activity with a concomitant increase in polymerization-dependent 5'-3' exonuclease activity.

The exonuclease function of the *T. litoralis* DNA polymerase was compared to those of well-characterized exonuclease functions of other polymerases as the deoxynucleotide concentration was increased from 10 uM to 100 uM. The exonuclease activity was measured as described in (1) with an incubation period of 30 minutes. As summarized in Table 2, the *T. litoralis* DNA polymerase responded to increases in deoxynucleotide levels similarly to a polymerase known to possess a 3'-5' proofreading exonuclease (Klenow fragment of *E. coli* DNA Pol. I). This response was in contradiction to that of a polymerase known not to possess this proofreading function, Taq DNA polymerase. This polymerase responded to an increase in deoxynucleotide levels with an increase in exonuclease function due to its 5'-3' exonuclease activity.

3. Response of *T. litoralis* DNA Polymerase to Alteration from a Balanced Deoxynucleotide State to an Unbalanced State Polymerization is dependent on equal levels of all four deoxynucleotides present during DNA synthesis.

If the deoxynucleotide levels are not equal, polymerases have decreased polymerization rates and are more likely to insert incorrect bases. Such conditions greatly increase proofreading 3'-5' exonuclease activities while decreasing 5'-3' exonuclease activities. Lehman, I. R., ARB (1967) 36:645.

The T. litoralis DNA polymerase was incubated with both balanced deoxynucleotide levels (30 uM) and two levels of imbalance characterized by dCTP present at 1/10 or 1/100 the level of the other three deoxynucleotides. The response of the T. litoralis DNA polymerase was then compared to that of three polymerases possessing either the 3'-5' or the 5'-3' exonuclease functions. All assays were performed as described in (1) except for dCTP concentrations listed below. As seen in Table 3 below, the T. litoralis DNA polymerase follows the expected behavior for a proofreading 3'-5' exonuclease-containing polymerase; an imbalance in deoxynucleotide pools increased the exonuclease activity in a similar manner as that of the proofreading polymerases of T4 DNA polymerase or Klenow fragment of E. coli DNA polymerase I. In contrast to this response, the exonuclease of the Taq DNA polymerase was not affected until the imbalance was heightened to the point that polymerization was inhibited.

4. Directionality of Exonuclease Activity

A proofreading exonuclease has a 3'-5' directionality on DNA while nonproofreading exonuclease associated with DNA polymerases have a 5'-3' directionality. To discern the direction of the exonuclease activity of T. litoralis DNA polymerase, the 5' blocked DNA of adenovirus was utilized. Since the 5' end of this DNA is blocked by protein, enzymic activities that are 5'-3' in directionality cannot digest this double-stranded DNA; however, enzymic activities that are 3'-5', such as exonuclease III or proofreading exonuclease-containing polymerases, can digest adenovirus DNA.

Twenty-five units of exonuclease III or 20 units of either T. litoralis DNA polymerase, T4 DNA polymerase (possessing a well characterized 3'-5' exonuclease activity), or Taq DNA polymerase (lacking such an activity) were incubated with 5 μg adenovirus DNA for time periods up to 30 minutes duration at either 37° C. (T4 polymerase and exonuclease III) or 70° C. (Taq polymerase and T. litoralis polymerase) in the presence of 70 mM tris-HCl pH 8.8 at 25° C., 2 mM MgCl₂ and 100 μg/ml BSA. At the end of each incubation time period, enzymic activity was stopped by phenol extraction of the adenovirus DNA, followed by HpaI digestion for one hour at 37° C. in 20 mM tris, pH 7.9 at 25° C., 10 mM Magnesium acetate 50 mM potassium acetate and 1 mM DTT. The DNA fragments were subjected to agarose gel electrophoresis and the resulting pattern of time-dependent degradation and subsequent loss of double-stranded DNA fragments were assessed.

The 3'-5' exonuclease activities of exonuclease III, of T. litoralis DNA polymerase and T4 DNA polymerase caused the disappearance of the double-strand DNA fragments originating from the 5' blocked end of the adenovirus DNA, indicating vulnerability of its 3' end. In contrast, the Taq DNA polymerase with its 5'-3' polymerization-dependent exonuclease activity, showed no disappearance of the DNA fragment.

EXAMPLE IX

Performance of T. litoralis DNA Polymerase in the PCR Process

The ability of the T. litoralis DNA polymerase to perform the polymerase chain reaction (PCR) was also examined. In 100 μl volumes containing the buffer described in Example IV, varying amounts of M13mp18 DNA cut by ClaI digestion, generating 2 fragments of 4355 bp and 2895 bp, were incubated with 200 ng of calf thymus DNA present as carrier DNA to decrease any nonspecific adsorption effects. The forward and reverse primers were present at 1 μM (forward primer=5'd(-CCAGCAAGGCCGATAGTTTGAGTT)3' (SEQ ID NO: 6) and the reverse primer=5'd(CG-CCAGGGTTTTCCCAGTCACGAC)3') (SEQ ID NO: 7). These primers flank a 1 kb DNA sequence on the 4355 bp fragment described above, with the sequence representing 14% of the total M13mp18 DNA. Also present were 200 μM each dNTP, 100 μg/ml BSA, 10% DMSO and 2.5 units of either T. aquaticus DNA polymerase (in the presence or absence of 0.5% NP40 and 0.05% Tween 20), or T. litoralis DNA polymerase (in the presence or absence of 0.10% Triton X-100). The initial cycle consisted of 5 min at 95° C., 5 min at 50° C. (during which polymerase and BSA additions were made) and 5 min at 70° C. The segments of each subsequent PCR cycle were the following: 1 min at 93° C., 1 min at 50° C. and 5 min at 70° C. After 0, 13, 23 and 40 cycles, 20 μl amounts of 100 μl volumes were removed and subjected to agarose gel electrophoresis

TABLE 2

| Amount | Type of DNA Polymerase | Acid-Soluble CPM (Exonuclease Activity) | | Effect on Hydrolysis with Increasing dNTPS |
|---|---|---|---|---|
| | | 10 uM dNTPS | 100 uM dNTPS | |
| 5 units | Taq Polymerase | 350 | 610 | 1.7 × increase |
| 5 units | Klenow fragment of E. coli Pol. I | 650 | 300 | 2.2 × decrease |
| 5 units | T. litoralis Polymerase | 180 | 110 | 1.6 × decrease |

TABLE 3

| Type of DNA Polymerase (5 units @) | Acid-soluble CPM (Exonuclease Activity) | | | |
|---|---|---|---|---|
| | no dNTPS | 30 uM dNTPS | 30 uM/3 uM* | 30 uM/0.3 uM** |
| Taq Polymerase | 338 | 2539 | 2243 | 656 |
| T4 Polymerase | ***46001 | 10418 | ***43850 | ***46585 |
| Klenow Fragment of E. coli Pol. I | 8757 | 408 | 1291 | 1755 |
| T. litoralis Polymerase | 8573 | 795 | 3471 | 3339 |

*3 uM dCTP, 30 uM all other dNTPs
**0.3 uM dCTP, 30 uM all other dNTPs
***nonlinear range of assay with ethidium bromide present to quantitate the amplification of the 1 kb DNA sequence.

Initial experiments with this target DNA sequence present at 28 ng and 2.8 ng established the ability of the *T. litoralis* DNA polymerase to catalyze the polymerase chain reaction; yields were comparable or not more than twofold greater than the seen with *T. aquaticus* DNA polymerase.

However, it was at the lower levels of target DNA sequence, 2.8 femtograms, that differences in polymerase function were most apparent. Under these conditions requiring maximal polymerase stability and/or efficiency at elongation of DNA during each cycle, the *T. litoralis* DNA polymerase produced greater than fourfold more amplified DNA than that of *T. aquaticus* DNA polymerase within 23 cycles.

This ability to amplify very small amounts of DNA with fewer cycles is important for many applications of PCR since employing large cycle numbers for amplification is associated with the generation of undesirable artifacts during the PCR process.

EXAMPLE X

Purification of Recombinant *T. litoralis* Intron-Encoded Endonuclease

*E. coli* NEB671 (ATCC No. 68447), grown as described in Example IV, were thawed (70 grams) and suspended in Buffer A containing 200 μg of lysozyme per ml to a final volume of 300 ml. The mixture was incubated at 37° C. for 2 minutes and then 75° C. for 30 minutes. The heated mixture was centrifuged at 22,000× g for 30 minutes and the supernatant was collected for further purification of the thermostable endonuclease. Since all of the nucleases from *E. coli* were inactivated by the heat treatment, the preparation at this stage could be used for characterization of the intron-encoded endonuclease. To separate this enzyme from the recombinant *T. litoralis* DNA polymerase also present in the 75° C. supernatant solution, the solution was passed through a DEAE-sepharose column (5 cm×5 cm, 100 ml bed volume) and washed with 200 ml of Buffer A. Essentially all of the DNA polymerase activity passes through the column while the endonuclease activity sticks. The endonuclease activity was eluted with a one liter linear gradient of NaCl from 0.1M to 0.8M formed in Buffer A. The endonuclease activity eluted at about 0.4M NaCl, and was assayed in a buffer containing 10 mM KCl, 20 mM Tris-HCl (pH 8.8 at 24° C.), 10 mM $(NH_4)_4SO_4$, 10 mM $MgSO_4$, 0.1% Triton X-100 and 1 μg of pBR322 DNA per 0.05 ml of reaction mixture. The reaction mixture was incubated at 75° C. and the extent of DNA cleavage was determined by agarose gel electrophorese. At lower temperatures little or no endonuclease activity was detected. The tubes containing the peak activity were pooled, dialyzed overnight against Buffer A and then applied to phosphocellulose column (2.5 cm×6.5 cm, 32 ml bed volume), washed with Buffer A and the endonuclease activity eluted with a linear gradient of NaCl from 0.1M to 1.5M formed in Buffer A. The enzyme eluted at about 0.8M NaCl. Active fractions were pooled and dialyzed overnight against Buffer A and then passed through a HPLC Mono-S column (Pharmacia) and eluted with a linear gradient of NaCl from 0.05M to 1.0M. The activity eluted as a single peak and was homogeneous by SDS-PAGE: a single 33–37 kd band was detected by Commasie blue staining and when this band was eluted from the gel and renatured it contained the only endonuclease activity detected on the gel.

The enzyme has preferred cutting sites on various DNAs. There are several fast cutting sites on lambda DNA and many slow sites. On the plasmid pBR322 the enzyme cuts three sites rapidly and a few other sites slowly on prolonged incubation. Two of the rapid sites on pBR322 have been sequenced:

Site at position 164:

| | |
|---|---|
| 5' TTGGTTATGCCGGTACTGCCGGCCTCTT 3' | (SEQ ID NO: 8) |
| 3' AACCAATACGGCCATGACGGCCGGAGAA 5' | (SEQ ID NO: 9) |

Site at position 2411:

| | |
|---|---|
| 5' TTGAGTGAGCTGATACCGCTCGCCGCAG 3' | (SEQ ID NO: 10) |
| 3' AACTCACTCGACTATGGCGAGCGGCGTC 5' | (SEQ ID NO: 11) |

Thus, the endonuclease from *T. litoralis* resembles other intron-encoded endonucleases reported from yeast in that their is a four base 3' extension at the cut site.

The thermostable endonuclease of the present invention can be used in genetic manipulation techniques where such activity is desired.

---

We claim:

1. A thermostable DNA polymerase endogenous to *Thermococcus litoralis*, wherein said polymerase is substantially free of 3'-5' exonuclease activity and is substantially free of *T. litoralis* nucleic acids.

2. The thermostable enzyme of claim 1, wherein said enzyme is expressed by *E. coli* NEB 681.

3. An isolated DNA fragment consisting essentially of an about 1.3 kb DNA region encoding the amino-terminal portion of a thermostable DNA polymerase endogenous to *Thermococcus litoralis*.

4. The isolated DNA fragment of claim 3, wherein the isolated DNA comprises nucleotides 1 to 1274 of SEQ ID NO: 1.

5. A vector containing the isolated DNA fragment of claim 3.

6. The vector of claim 5, wherein such vector is bacteriophage NEB 618.

7. An isolated DNA fragment consisting essentially of about a 1.6 kb DNA region encoding the intermediate portion of a thermostable DNA polymerase endogenous to *Thermococcus litoralis* exclusive of about a 5' terminal 1.3 kb and about a 3' terminal 1.9 kb portions of the coding region for the DNA polymerase.

8. The isolated DNA fragment of claim 7, wherein the isolated DNA comprises nucleotides 1269 to 2856 of SEQ ID NO: 1.

9. A vector containing the isolated DNA fragment of claim 8.

10. The vector of claim 9, wherein such vector is bacteriophage NEB 620.

11. An isolated DNA fragment consisting essentially of a 1.9 kb DNA region encoding a portion of the carboxyl terminal of a thermostable DNA polymerase endogenous to *Thermococcus litoralis*.

12. The isolated DNA fragment of claim 11, wherein the isolated DNA comprises nucleotides 2851 to 4771 of SEQ ID NO: 1.

13. A vector containing the isolated DNA fragment of claim 11.

14. The vector of claim 13, wherein such vector is plasmid V153-2.

15. A vector comprising the isolated DNA fragment of claim 3 operably linked in the proper reading frame with the isolated DNA fragment of claim 17 to product *Thermococcus litoralis* DNA polymerase or a portion thereof.

16. The vector of claim 15, further comprising the isolated DNA fragment of claim 11 operably linked in the proper reading frame to produce *Thermococcus litoralis* DNA polymerase or a portion thereof.

17. An isolated DNA fragment consisting essentially of a DNA region encoding a thermostable DNA polymerase endogenous to *Thermococcus litoralis*.

18. A vector containing the DNA sequence of claim 17.

19. A microbial host transformed by the vector of claim 18.

20. An isolated DNA fragment according to claim 17 contained within an approximately 14 kb BamHI restriction fragment of bacteriophage NEB 619.

21. The isolated DNA fragment according to claim 17, comprising an approximately 4 kb BamHI/NdeI restriction fragment of plasmid pPR969.

22. The isolated DNA fragment of claim 17, comprising the DNA fragment of SEQ ID NO: 1.

23. The isolated DNA fragment of claim 22, wherein nucleotides 1776 to 3389 have been deleted.

24. A vector containing the DNA of claim 22.

25. A vector containing the DNA of claim 23.

26. The vector of claim 25, wherein said vector is plasmid V174-1B1.

27. The vector of claim 25, wherein said vector is plasmid pPR969.

28. A microbial host transformed with the vector of claim 26 or claim 27.

29. The transformant of claim 28, wherein said transformant is *E. coli* NEB 671.

30. The transformant of claim 28, wherein said transformant is *E. coli* NEB687.

31. A process for the preparation of *Thermococcus litoralis* DNA polymerase comprising culturing the transformed microbial host of any of claims 28, 29, or 30 under conditions suitable for the expression of *Thermococcus litoralis* DNA polymerase and recovering *Thermococcus litoralis* DNA polymerase.

32. A method for producing *Thermococcus litoralis* DNA polymerase comprising the steps of
 (a) purifying total DNA from *Thermococcus litoralis*;
 (b) isolating DNA from the total DNA of step (a) which codes for the DNA polymerase;
 (c) removing an about 1.6 kb intervening DNA from said isolated DNA of step (b) wherein said intervening DNA corresponds to a region from about nucleotides 1761-1775 to about nucleotides 3384-3392 as depicted in SEQ ID NO: 1, whereby upon removal a consensus region corresponding to consensus region III of FIG. No. 7 is formed;
 (d) ligating the DNA of step (c) into an appropriate vector;
 (e) transforming a host with the vector of step (d);
 (f) cultivating the transformed host of step (e) under conditions suitable for expression of the *T. litoralis* DNA polymerase;
 (g) recovering the *Thermococcus litoralis* DNA polymerase.

33. The method of claim 32, wherein the isolated DNA consists essentially of the DNA of SEQ ID NO: 1.

34. The method of claim 32, wherein said intervening DNA corresponds to a region from nucleotide 1773-1775 to nucleotide 3386-3389 as depicted in SEQ ID NO: 1.

35. The method of claim 32, wherein the intervening DNA comprises nucleotides 1776 to 3389 of FIG. No. 6.

36. A substantially pure thermostable endonuclease endogenous to *Thermococcus litoralis* which cleaves double-stranded deoxynucleotide acid pBR322 at position 164 and positions 2411.

37. The thermostable endonuclease of claim 36, having a molecular weight of about 33,000–37,000 daltons.

38. The isolated DNA of claim 22, which further codes for the thermostable endonuclease of claim 36.

39. The isolated DNA of claim 38, wherein the coding sequence for the endonuclease starts at nucleotide 3534.

* * * * *

UNITED STATES PATENT AND TRADEMARK OFFICE
CERTIFICATE OF CORRECTION

PATENT NO. : 5,322,785
DATED : June 21, 1994
INVENTOR(S) : Comb, et al

Page 1 of 2

It is certified that error appears in the above-indentified patent and that said Letters Patent is hereby corrected as shown below:

Column 18, line 28, replace "VI17-1" with --V117-1--.

Column 18, line 32, replace "5," with --5'--.

Column 20, line 29, replace "pETI1c" with --pET11c--.

Column 24, line 3, replace "GCG ATC GCA" with --G<u>CG ATC G</u>CA--

Column 30, lines 36 and 37, replace:
"5' TTGGTTATGCCGGTACTGCCGGCCTCTT 3'
3' AACCAATACGGCCATGACGGCCGGAGAA 5'"

with --5' TTGGTTATGCCGGTAC<sup>v</sup>TGCCGGCCTCTT 3'
3' AACCAATACGGC<sub>∧</sub>CATGACGGCCGGAGAA 5' --

UNITED STATES PATENT AND TRADEMARK OFFICE
CERTIFICATE OF CORRECTION

PATENT NO. : 5,322,785
DATED : June 21, 1994
INVENTOR(S) : Comb, et al

It is certified that error appears in the above-indentified patent and that said Letters Patent is hereby corrected as shown below:

Column 30, lines 39 and 40, replace:

```
"5' TTGAGTGAGCTGATACCGCTCGCCGCAG 3'
 3' AACTCACTCGACTATGGCGAGCGGCGTC 5' "
``` with -- 5'  TTGAGTGAGCTGATAC^CGCTCGCCGCAG  3'
     3'  AACTCACTCGAC₍TATGGCGAGCGGCGTC  5'  --

Signed and Sealed this

Twenty-first Day of February, 1995

BRUCE LEHMAN

Attest:

Attesting Officer

Commissioner of Patents and Trademarks

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
( A ) LENGTH: 5837 base pairs
( B ) TYPE: nucleic acid
( C ) STRANDEDNESS: double
( D ) TOPOLOGY: linear ( x i ) SEQUENCE DESCRIPTION: SEQ ID NO:1:

GAATTCGCGA TAAAATCTAT TTTCTTCCTC CATTTTTCAA TTTCAAAAAC GTAAGCATGA     60

-continued

```
GCCAAACCTC TCGCCCTTTC TCTGTCCTTC CCGCTAACCC TCTTGAAAAC TCTCTCCAAA      120
GCATTTTTTG ATGAAAGCTC ACGCTCCTCT ATGAGGGTCA GTATATCTGC AATGAGTTCG      180
TGAAGGGTTA TTCTGTAGAA CAACTCCATG ATTTTCGATT TGGATGGGGG TTTAAAAATT      240
TGGCGGAACT TTTATTTAAT TTGAACTCCA GTTTATATCT GGTGGTATTT ATGATACTGG      300
ACACTGATTA CATAACAAAA GATGGCAAGC CTATAATCCG AATTTTTAAG AAAGAGAACG      360
GGGAGTTTAA AATAGAACTT GACCCTCATT TTCAGCCCTA TATATATGCT CTTCTCAAAG      420
ATGACTCCGC TATTGAGGAG ATAAAGGCAA TAAAGGGCGA GAGACATGGA AAAACTGTGA      480
GAGTGCTCGA TGCAGTGAAA GTCAGGAAAA AATTTTTGGG AAGGGAAGTT GAAGTCTGGA      540
AGCTCATTTT CGAGCATCCC CAAGACGTTC CAGCTATGCG GGCAAAATA AGGGAACATC       600
CAGCTGTGGT TGACATTTAC GAATATGACA TACCCTTTGC CAAGCGTTAT CTCATAGACA      660
AGGGCTTGAT TCCCATGGAG GGAGACGAGG AGCTTAAGCT CCTTGCCTTT GATATTGAAA      720
CGTTTTATCA TGAGGGAGAT GAATTTGGAA AGGGCGAGAT AATAATGATT AGTTATGCCG      780
ATGAAGAAGA GGCCAGAGTA ATCACATGGA AAAATATCGA TTTGCCGTAT GTCGATGTTG      840
TGTCCAATGA AAGAGAAATG ATAAAGCGTT TTGTTCAAGT TGTTAAAGAA AAAGACCCCG      900
ATGTGATAAT AACTTACAAT GGGGACAATT TTGATTTGCC GTATCTCATA AAACGGGCAG      960
AAAAGCTGGG AGTTCGGCTT GTCTTAGGAA GGGACAAAGA ACATCCCGAA CCCAAGATTC     1020
AGAGGATGGG TGATAGTTTT GCTGTGGAAA TCAAGGGTAG AATCCACTTT GATCTTTTCC     1080
CAGTTGTGCG AAGGACGATA AACCTCCCAA CGTATACGCT TGAGGCAGTT TATGAAGCAG     1140
TTTTAGGAAA AACCAAAAGC AAATTAGGAG CAGAGGAAAT TGCCGCTATA TGGGAAACAG     1200
AAGAAAGCAT GAAAAAACTA GCCCAGTACT CAATGGAAGA TGCTAGGGCA ACGTATGAGC     1260
TCGGGAAGGA ATTCTTCCCC ATGGAAGCTG AGCTGGCAAA GCTGATAGGT CAAAGTGTAT     1320
GGGACGTCTC GAGATCAAGC ACCGGCAACC TCGTGGAGTG GTATCTTTTA AGGGTGGCAT     1380
ACGCGAGGAA TGAACTTGCA CCGAACAAAC CTGATGAGGA AGAGTATAAA CGGCGCTTAA     1440
GAACAACTTA CCTGGGAGGA TATGTAAAAG AGCCAGAAAA AGGTTTGTGG AAAATATCA      1500
TTTATTTGGA TTTCCGCAGT CTGTACCCTT CAATAATAGT TACTCACAAC GTATCCCCAG     1560
ATACCCTTGA AAAAGAGGGC TGTAAGAATT ACGATGTTGC TCCGATAGTA GGATATAGGT     1620
TCTGCAAGGA CTTTCCGGGC TTTATTCCCT CCATACTCGG GGACTTAATT GCAATGAGGC     1680
AAGATATAAA GAAGAAAATG AAATCCACAA TTGACCCGAT CGAAAAGAAA ATGCTCGATT     1740
ATAGGCAAAG GGCTATTAAA TTGCTTGCAA ACAGCATCTT ACCCAACGAG TGGTTACCAA     1800
TAATTGAAAA TGGAGAAATA AAATTCGTGA AAATTGGCGA GTTTATAAAC TCTTACATGG     1860
AAAAACAGAA GGAAAACGTT AAAACAGTAG AGAATACTGA AGTTCTCGAA GTAAACAACC     1920
TTTTTGCATT CTCATTCAAC AAAAAAATCA AAGAAAGTGA AGTCAAAAAA GTCAAAGCCC     1980
TCATAAGACA TAAGTATAAA GGGAAAGCTT ATGAGATTCA GCTTAGCTCT GGTAGAAAAA     2040
TTAACATAAC TGCTGGCCAT AGTCTGTTTA CAGTTAGAAA TGGAGAAATA AAGGAAGTTT     2100
CTGGAGATGG GATAAAAGAA GGTGACCTTA TTGTAGCACC AAAGAAAATT AAACTCAATG     2160
AAAAAGGGGT AAGCATAAAC ATTCCCGAGT TAATCTCAGA TCTTTCCGAG AAGAAACAG      2220
CCGACATTGT GATGACGATT TCAGCCAAGG GCAGAAAGAA CTTCTTTAAA GGAATGCTGA     2280
GAACTTTAAG GTGGATGTTT GGAGAAGAAA ATAGAAGGAT AAGAACATTT AATCGCTATT     2340
TGTTCCATCT CGAAAAACTA GGCCTTATCA AACTACTGCC CCGCGGATAT GAAGTTACTG     2400
ACTGGGAGAG ATTAAAGAAA TATAAACAAC TTTACGAGAA GCTTGCTGGA AGCGTTAAGT     2460
ACAACGGAAA CAAGAGAGAG TATTTAGTAA TGTTCAACGA GATCAAGGAT TTTATATCTT     2520
```

```
ACTTCCCACA AAAAGAGCTC GAAGAATGGA AAATTGGAAC TCTCAATGGC TTTAGAACGA    2580
ATTGTATTCT CAAAGTCGAT GAGGATTTTG GGAAGCTCCT AGGTTACTAT GTTAGTGAGG    2640
GCTATGCAGG TGCACAAAAA AATAAAACTG GTGGTATCAG TTATTCGGTG AAGCTTTACA    2700
ATGAGGACCC TAATGTTCTT GAGAGCATGA AAAATGTTGC AGAAAAATTC TTTGGCAAGG    2760
TTAGAGTTGA CAGAAATTGC GTAAGTATAT CAAAGAAGAT GGCATACTTA GTTATGAAAT    2820
GCCTCTGTGG AGCATTAGCC GAAAACAAGA GAATTCCTTC TGTTATACTC ACCTCTCCCG    2880
AACCGGTACG GTGGTCATTT TTAGAGGCGT ATTTTACAGG CGATGGAGAT ATACATCCAT    2940
CAAAAAGGTT TAGGCTCTCA ACAAAAGCG AGCTCCTTGC AAATCAGCTT GTGTTCTTGC    3000
TGAACTCTTT GGGAATATCC TCTGTAAAGA TAGGCTTTGA CAGTGGGGTC TATAGAGTGT    3060
ATATAAATGA AGACCTGCAA TTTCCACAAA CGTCTAGGGA GAAAACACA TACTACTCTA    3120
ACTTAATTCC CAAAGAGATC CTTAGGGACG TGTTTGGAAA AGAGTTCCAA AGAACATGA    3180
CGTTCAAGAA ATTTAAAGAG CTTGTTGACT CTGGAAAACT TAACAGGGAG AAAGCCAAGC    3240
TCTTGGAGTT CTTCATTAAT GGAGATATTG TCCTTGACAG AGTCAAAAGT GTTAAAGAAA    3300
AGGACTATGA AGGGTATGTC TATGACCTAA GCGTTGAGGA TAACGAGAAC TTTCTTGTTG    3360
GTTTTGGTTT GCTCTATGCT CACAACAGCT ATTACGGCTA TATGGGGTAT CCTAAGGCAA    3420
GATGGTACTC GAAGGAATGT GCTGAAAGCG TTACCGCATG GGGGAGACAC TACATAGAGA    3480
TGACGATAAG AGAAATAGAG GAAAAGTTCG GCTTTAAGGT TCTTTATGCG GACAGTGTCT    3540
CAGGAGAAAG TGAGATCATA ATAAGGCAAA ACGGAAAGAT TAGATTTGTG AAAATAAAGG    3600
ATCTTTTCTC TAAGGTGGAC TACAGCATTG GCGAAAAGA ATACTGCATT CTCGAAGGTG    3660
TTGAAGCACT AACTCTGGAC GATGACGGAA AGCTTGTCTG GAAGCCCGTC CCCTACGTGA    3720
TGAGGCACAG AGCGAATAAA AGAATGTTCC GCATCTGGCT GACCAACAGC TGGTATATAG    3780
ATGTTACTGA GGATCATTCT CTCATAGGCT ATCTAAACAC GTCAAAAACG AAAACTGCCA    3840
AAAAAATCGG GGAAAGACTA AAGGAAGTAA AGCCTTTTGA ATTAGGCAAA GCAGTAAAAT    3900
CGCTCATATG CCCAAATGCA CCGTTAAAGG ATGAGAATAC CAAAACTAGC GAAATAGCAG    3960
TAAAATTCTG GGAGCTCGTA GGATTGATTG TAGGAGATGG AAACTGGGGT GGAGATTCTC    4020
GTTGGGCAGA GTATTATCTT GGACTTTCAA CAGGCAAAGA TGCAGAAGAG ATAAAGCAAA    4080
AACTTCTGGA ACCCCTAAAA ACTTATGGAG TAATCTCAAA CTATTACCCA AAAACGAGA    4140
AAGGGGACTT CAACATCTTG GCAAGAGCC TTGTAAAGTT TATGAAAAGG CACTTTAAGG    4200
ACGAAAAAGG AAGACGAAAA ATTCCAGAGT TCATGTATGA GCTTCCGGTT ACTTACATAG    4260
AGGCATTTCT ACGAGGACTG TTTTCAGCTG ATGGTACTGT AACTATCAGG AAGGGAGTTC    4320
CAGAGATCAG GCTAACAAAC ATTGATGCTG ACTTCTAAG GGAAGTAAGG AAGCTTCTGT    4380
GGATTGTTGG AATTTCAAAT TCAATATTTG CTGAGACTAC TCCAAATCGC TACAATGGTG    4440
TTTCTACTGG AACCTACTCA AAGCATCTAA GGATCAAAAA TAAGTGGCGT TTTGCTGAAA    4500
GGATAGGCTT TTTAATCGAG AGAAAGCAGA AGAGACTTTT AGAACATTTA AAATCAGCGA    4560
GGGTAAAAAG GAATACCATA GATTTGGCT TTGATCTTGT GCATGTGAAA AAAGTCGAAG    4620
AGATACCATA CGAGGGTTAC GTTTATGACA TTGAAGTCGA AGAGACGCAT AGGTTCTTTG    4680
CAAACAACAT CCTGGTACAC AATACTGACG GCTTTTATGC CACAATACCC GGGGAAAAGC    4740
CTGAACTCAT TAAAAAGAAA GCCAAGGAAT TCCTAAACTA CATAAACTCC AAACTTCCAG    4800
GTCTGCTTGA GCTTGAGTAT GAGGGCTTTT ACTTGAGAGG ATTCTTTGTT ACAAAAAAGC    4860
GCTATGCAGT CATAGATGAA GAGGGCAGGA TAACAACAAG GGGCTTGGAA GTAGTAAGGA    4920
GAGATTGGAG TGAGATAGCT AAGGAGACTC AGGCAAAGGT TTTAGAGGCT ATACTTAAAG    4980
```

```
AGGGAAGTGT TGAAAAAGCT GTAGAAGTTG TTAGAGATGT TGTAGAGAAA ATAGCAAAAT      5040

ACAGGGTTCC ACTTGAAAAG CTTGTTATCC ATGAGCAGAT TACCAGGGAT TTAAAGGACT      5100

ACAAAGCCAT TGGCCCTCAT GTCGCGATAG CAAAAAGACT TGCCGCAAGA GGGATAAAAG      5160

TGAAACCGGG CACAATAATA AGCTATATCG TTCTCAAAGG GAGCGGAAAG ATAAGCGATA      5220

GGGTAATTTT ACTTACAGAA TACGATCCTA GAAAACACAA GTACGATCCG GACTACTACA      5280

TAGAAAACCA AGTTTTGCCG GCAGTACTTA GGATACTCGA AGCGTTTGGA TACAGAAAGG      5340

AGGATTTAAG GTATCAAAGC TCAAAACAAA CCGGCTTAGA TGCATGGCTC AAGAGGTAGC      5400

TCTGTTGCTT TTTAGTCCAA GTTTCTCCGC GAGTCTCTCT ATCTCTCTTT TGTATTCTGC      5460

TATGTGGTTT TCATTCACTA TTAAGTAGTC CGCCAAAGCC ATAACGCTTC CAATTCCAAA      5520

CTTGAGCTCT TTCCAGTCTC TGGCCTCAAA TTCACTCCAT GTTTTGGAT CGTCGCTTCT       5580

CCCTCTTCTG CTAAGCCTCT CGAATCTTTT TCTTGGCGAA GAGTGTACAG CTATGATGAT      5640

TATCTCTTCC TCTGGAAACG CATCTTTAAA CGTCTGAATT TCATCTAGAG ACCTCACTCC      5700

GTCGATTATA ACTGCCTTGT ACTTCTTTAG TAGTTCTTTT ACCTTTGGGA TCGTTAATTT      5760

TGCCACGGCA TTGTCCCCAA GCTCCTGCCT AAGCTGAATG CTCACACTGT TCATACCTTC      5820

GGGAGTTCTT GGGATCC                                                    5837
```

(2) INFORMATION FOR SEQ ID NO:2:

(i) SEQUENCE CHARACTERISTICS:
        (A) LENGTH: 18 amino acids
        (B) TYPE: amino acid
        (C) STRANDEDNESS: single
        (D) TOPOLOGY: linear (xi) SEQUENCE DESCRIPTION: SEQ ID NO:2:

```
Asp Tyr Arg Gln Arg Ala Ile Lys Leu Leu Ala Asn Ser Ile Leu Pro
 1               5                  10                  15

Asn Glu
```

(2) INFORMATION FOR SEQ ID NO:3:

(i) SEQUENCE CHARACTERISTICS:
        (A) LENGTH: 33 amino acids
        (B) TYPE: amino acid
        (C) STRANDEDNESS: single
        (D) TOPOLOGY: linear (xi) SEQUENCE DESCRIPTION: SEQ ID NO:3:

```
Leu Leu Tyr Ala His Asn Ser Tyr Tyr Gly Tyr Met Gly Tyr Pro Lys
 1               5                  10                  15

Ala Arg Trp Tyr Ser Lys Glu Cys Ala Glu Ser Val Thr Ala Trp Gly
                20                  25                  30

Arg
```

(2) INFORMATION FOR SEQ ID NO:4:

(i) SEQUENCE CHARACTERISTICS:
        (A) LENGTH: 78 base pairs
        (B) TYPE: nucleic acid
        (C) STRANDEDNESS: single
        (D) TOPOLOGY: linear (xi) SEQUENCE DESCRIPTION: SEQ ID NO:4:

```
CGAAAAGAAA ATGCTCGATT ATAGGCAAAG GGCTATTAAA TTGCTAGCAA ACAGCTATTA       60

CGGCTATATG GGGTACCC                                                     78
```

( 2 ) INFORMATION FOR SEQ ID NO:5:

( i ) SEQUENCE CHARACTERISTICS:
       ( A ) LENGTH: 83 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:5:

TTAGGGTACC CCATATAGCC GTAATAGCTG TTTGCTAGCA ATTTAATAGC CCTTTGCCTA        60

TAATCGAGCA TTTTCTTTTC GAT                                               83

( 2 ) INFORMATION FOR SEQ ID NO:6:

( i ) SEQUENCE CHARACTERISTICS:
       ( A ) LENGTH: 24 base pairs
       ( B ) TYPE: nucleic acid
       ( C ) STRANDEDNESS: unknown
       ( D ) TOPOLOGY: unknown ( x i ) SEQUENCE DESCRIPTION: SEQ ID NO:6:

CCAGCAAGGC CGATAGTTTG AGTT                                              24

( 2 ) INFORMATION FOR SEQ ID NO:7:

( i ) SEQUENCE CHARACTERISTICS:
       ( A ) LENGTH: 24 base pairs
       ( B ) TYPE: nucleic acid
       ( C ) STRANDEDNESS: unknown
       ( D ) TOPOLOGY: unknown ( x i ) SEQUENCE DESCRIPTION: SEQ ID NO:7:

CGCCAGGGTT TTCCCAGTCA CGAC                                              24

( 2 ) INFORMATION FOR SEQ ID NO:8:

( i ) SEQUENCE CHARACTERISTICS:
       ( A ) LENGTH: 28 base pairs
       ( B ) TYPE: nucleic acid
       ( C ) STRANDEDNESS: unknown
       ( D ) TOPOLOGY: unknown ( x i ) SEQUENCE DESCRIPTION: SEQ ID NO:8:

TTGGTTATGC CGGTACTGCC GGCCTCTT                                          28

( 2 ) INFORMATION FOR SEQ ID NO:9:

( i ) SEQUENCE CHARACTERISTICS:
       ( A ) LENGTH: 28 base pairs
       ( B ) TYPE: nucleic acid
       ( C ) STRANDEDNESS: unknown
       ( D ) TOPOLOGY: unknown ( x i ) SEQUENCE DESCRIPTION: SEQ ID NO:9:

AAGAGGCCGG CAGTACCGGC ATAACCAA                                          28

( 2 ) INFORMATION FOR SEQ ID NO:10:

( i ) SEQUENCE CHARACTERISTICS:
       ( A ) LENGTH: 28 base pairs
       ( B ) TYPE: nucleic acid
       ( C ) STRANDEDNESS: unknown
       ( D ) TOPOLOGY: unknown ( x i ) SEQUENCE DESCRIPTION: SEQ ID NO:10:

TTGAGTGAGC TGATACCGCT CGCCGCAG                                          28

( 2 ) INFORMATION FOR SEQ ID NO:11:

( i ) SEQUENCE CHARACTERISTICS:
 ( A ) LENGTH: 28 base pairs
 ( B ) TYPE: nucleic acid
 ( C ) STRANDEDNESS: unknown
 ( D ) TOPOLOGY: unknown ( x i ) SEQUENCE DESCRIPTION: SEQ ID NO:11:

CTGCGGCGAG CGGTATCAGC TCACTCAA  28